US011202421B2

(12) United States Patent
Kock et al.

(10) Patent No.: US 11,202,421 B2
(45) Date of Patent: *Dec. 21, 2021

(54) ***PERONOSPORA* RESISTANCE IN *SPINACIA OLERACEA***

(71) Applicant: RIJK ZWAAN ZAADTEELT EN ZAADHANDEL B.V., De Lier (NL)

(72) Inventors: Vincent Laurens Adrianus Kock, De Lier (NL); Johannes Geert Jan Feitsma, De Lier (NL); Raoul Jacobus Johannes Maria Frijters, De Lier (NL)

(73) Assignee: RIJK ZWAAN ZAADTEELT EN ZAADHANDEK B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/361,451

(22) Filed: Mar. 22, 2019

(65) Prior Publication Data

US 2020/0017875 A1 Jan. 16, 2020

Related U.S. Application Data

(63) Continuation-in-part of application No. PCT/EP2017/074810, filed on Sep. 29, 2017.

(30) Foreign Application Priority Data

Sep. 30, 2016 (WO) .................. PCT/EP2016/073505

(51) Int. Cl.
| | | |
|---|---|---|
| *A01H 5/12* | (2018.01) | |
| *A01H 6/02* | (2018.01) | |
| *C12N 15/82* | (2006.01) | |
| *C12Q 1/6895* | (2018.01) | |

(52) U.S. Cl.
CPC .............. *A01H 5/12* (2013.01); *A01H 6/028* (2018.05); *C12N 15/8282* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| 9,121,029 B2 | 9/2015 | Van Damme et al. |
| 9,265,275 B2 | 2/2016 | Braber |
| 9,402,363 B1* | 8/2016 | Feitsma et al. ........... A01H 5/12 |
| 10,017,781 B2 | 7/2018 | Torjek et al. |
| 10,633,670 B2* | 4/2020 | Kock et al. ........ C12N 15/8282 |
| 2005/0183160 A1 | 6/2005 | Torisky et al. |
| 2007/0204368 A1 | 8/2007 | Dale |
| 2009/0300786 A1 | 12/2009 | Baerends |
| 2009/0300788 A1 | 12/2009 | Baerends |
| 2010/0031385 A1 | 2/2010 | Baerends |
| 2012/0054894 A1 | 3/2012 | Braber |
| 2013/0055422 A1 | 2/2013 | Baerends |
| 2013/0055454 A1 | 2/2013 | Braber |
| 2013/0230635 A1* | 9/2013 | den Braber ........ C12N 15/8282 426/615 |
| 2014/0065287 A1 | 3/2014 | Braber |
| 2014/0068799 A1 | 3/2014 | Braber |
| 2014/0068801 A1 | 3/2014 | Braber |
| 2014/0068804 A1 | 3/2014 | Braber |
| 2014/0068805 A1 | 3/2014 | Braber |
| 2014/0068806 A1 | 3/2014 | Braber |
| 2015/0082483 A1* | 3/2015 | Dijkstra ................... A01H 5/12 800/279 |
| 2015/0101073 A1 | 4/2015 | Brugmans |
| 2015/0240256 A1 | 8/2015 | Brugmans et al. |
| 2016/0152999 A1 | 6/2016 | Torjek et al. |
| 2016/0177330 A1* | 6/2016 | Dijkstra ............. C12N 15/8282 800/265 |
| 2017/0027126 A1 | 2/2017 | Dijkstra |
| 2017/0027127 A1 | 2/2017 | Dijkstra |
| 2017/0127641 A1 | 5/2017 | De Visser |
| 2017/0127642 A1 | 5/2017 | De Visser |

(Continued)

FOREIGN PATENT DOCUMENTS

| EP | 2 848 114 A1 | 3/2015 |
| EP | 2 912 940 A1 | 9/2015 |

(Continued)

OTHER PUBLICATIONS

NCBI Blast (2020) SEQ ID No. 8 v. Patent database.*
Correll et al. (2011) Eur J Plant Pathol 129:193-205.*
Qi & Innes (2013) Front Immunol 4:348.*
Bentham et al. (2017) Annals Bot 119:689-702.*
Sukarta et al. (2016) Sem Cell Devol Biol 56:134-49.*
Dodds et al. (2001) Plant Cell 13:163-78.*
Chakraborty et al. (2018) Plant Sci 269:85-93.*
Eitas & Dangl (2010) Curr Opin Plant Biol 13:472-77.*
She et al. (2018) Theor Appl Genet 131:2529-41.*
Irish et al. (2007) Plant Dis 91:1392-96.*

(Continued)

*Primary Examiner* — Russell T Boggs
(74) *Attorney, Agent, or Firm* — Duane Morris LLP; Thomas J. Kowalski; Deborah L. Lu

(57) ABSTRACT

The present invention relates to an allele designated alpha-WOLF 8 which confers resistance to at least one *Peronospora farinosa* f. Sp. *spinacea* race, wherein the protein encoded by said allele is a CC-NB S-LRR protein that comprises in its amino acid sequence: a) the motif "MAEI-GYSVC" (SEQ ID NO: 15) at its N-terminus; and b) the motif "KWMCLR" (SEQ ID NO: 16); and wherein the LRR domain of the protein has in order of increased preference at least 92%, 93%, 94%, 95%, 96%, 97%, 98%, 99%, 100% sequence similarity to SEQ ID NO: 12. When the allele is homozygously present in a spinach plant confers complete resistance to *Peronospora farinosa* f. Sp. *spinacea* races pfs:1, pfs:2, pfs:6, pfs:8 and pfs:15, and isolate US1508, and confers intermediate resistance to pfs:5, pfs:10 and pfs:16, and does not confer resistance to pfs:3, pfs:4, pfs:7, pfs:9, pfs:11, pfs:12, pfs:13 and pfs:14.

4 Claims, No Drawings

Specification includes a Sequence Listing.

(56) References Cited

U.S. PATENT DOCUMENTS

| | | | |
|---|---|---|---|
| 2017/0327839 A1* | 11/2017 | Feitsma | A01H 5/12 |
| 2018/0042198 A1 | 2/2018 | Feitsman | |
| 2019/0127753 A1* | 5/2019 | Kock et al. | A01H 5/12 |

FOREIGN PATENT DOCUMENTS

| | | |
|---|---|---|
| WO | 2007/051483 A1 | 5/2007 |
| WO | 2013/064436 A1 | 5/2013 |
| WO | 2015/036378 A1 | 3/2015 |
| WO | 2015/036469 A1 | 3/2015 |
| WO | 2015/171603 A1 | 11/2015 |
| WO | 2018/059653 A1 | 4/2018 |

OTHER PUBLICATIONS

Adam Bentham, et al., Animal NLRs Provide Structural Insights into Plant NLR Function, Annals of Botany (2017) 119:689-702.

Joydeep Chakraborty, et al., Functional Diversification of Structurally Alike NLR Proteins in Plants, Plant Science (2018) 269:85-93.

Peter N. Dodds, et al., Six Amino Acid Changes Confined to the Leucine-Rich Repeat β-Strand/βTurn Motif Determine the Difference between the P and P2 Rust Resistance Specificities in Flax, The Plant Cell (Jan. 2001) vol. 13, p. 163-178.

Timothy K. Eitas, et al., NB-LRR Proteins: Pairs, Pieces, Perception, Partners, and Pathways, Current Opinion in Plant Biology (2010) 13:472-477.

Genbank Accesssion No. XP_021842255, Aug. 1, 2017.

Haiwei H. Guo, et al., Protein tolerance to Random Amino Acid Change. PNAS (Jun. 22. 2004) vol. 101, No. 25, p. 9205-9210.

Charlotte Hallavant, et al., The First Archaeobotanical Evidence of *Spinacia Oleracea* L. (Spinach) in Late 12th-mid 13th Century A.D. France, French National Centre for Scientific Research, Article: Vegetation History and Archaeobotany, Published online May 21, 2013.

B. M. Irish, et al., Three New Races of the Spinach Downy Mildew Pathogen Identified by a Modified Set of Spinach Differentials, Plant Disease (Nov. 2007) vol. 91, No. 11. p. 1392-1396.

B. M. Irish, et al., Characterization of a Resistance Locus (Pfs-1) to the Spinach Downy Mildew Pathogen (*Peronospora farinosa* f. sp. *spinaciae*) and Development of a Molecular Marker Linked to Pfs-1, Phytopathology (2008) vol. 98, No. 8, p. 894-900.

Simona Proietti, et al., Increase of Ascorbic Acid Content and Nutritional Quality in Spinach Leaves During Physiological Acclimation to Low Temperature, Plant Physiology and Biochemistry (2009) vol. 47, p. 717-723.

Dong Qi, et al., Recent Advances in Plant NLR Structure, Function, Localization, and Signaling, Frontiers in Immunology (2013) vol. 4, Article 348, p. 1-10.

Hongbing She, et al., Fine Mapping and Candidate Gene Screening of the Downy Mildew Resistance Gene RPF1 in Spinach, Theoretical and Applied Genetics (2018) 131:2529-2541.

Octavina C.A. Sukarta, et al., Structure-Informed Insights for NLR Functioning in Plant Immunity, Seminars in Cell & Developmental Biology (2016) 56:134-149.

Yanming Yang, et al., Transgenic Spinach Plants Expressing the Coat Protein of Cucumber Mosaic Virus, In Vitro Cell Dev. Biol.-Plant (1997) 33:200-204.

Feng Chunda, et al., Construction of a Spinach Bacterial Artificial Chromosome (BAC) Library as a Resource for Gene Identification and Marker Development, Plant Molecular Biology Reporter (May 16, 2015) vol. 33, No. 6, p. 1996-2005.

Feng, et al., Identification of New Races and Deviating Strains of the Spinach Downy Mildew Pathogen *Peronospora farinosa* f. sp, *spinaciae*, Plant Disease (Jan. 2014) 98(1): 145-152.

Merriam Webster Definition of "as" Sep. 27, 2016.

2011 APS-IPPC Joint Meeting Abstracts of Presentations, Phytopathology (2011) 101(6) Supplemental, S1, S52.

J.C. Correll, et al., Spinach: Better Management of Downy Mildew and White Rust Through Genomics, Eur. J. Plant Pathology (Dec. 4, 2010) 129:193-205.

International Search Report dated Jan. 3, 2018 in PCT/EP2017/074810.

* cited by examiner

PERONOSPORA RESISTANCE IN *SPINACIA OLERACEA*

RELATED APPLICATIONS AND INCORPORATION BY REFERENCE

This application is a continuation-in-part application of international patent application Serial No. PCT/EP2017/074810 filed 29 Sep. 2017, which published as PCT Publication No. WO 2018/060445 on Apr. 5, 2018, which claims benefit of international patent application Serial No. PCT/EP2016/073505 filed 30 Sep. 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named 00419Sequence_Listing.txt and is 68 bytes in size.

FIELD OF THE INVENTION

The invention relates to an allele capable of conferring resistance to a spinach plant against multiple *Peronospora farinosa* f sp. *spinaciae* races. The invention also relates to a spinach plant, to propagation material of said spinach plant, to a cell of said spinach plant, and to seed of said spinach plant carrying the allele. The invention further relates to a method of producing a spinach plant carrying the allele and to the use of the allele in breeding to confer resistance against *Peronospora farinosa* f. sp. *spinaciae*.

BACKGROUND OF THE INVENTION

Downy mildew (*Peronospora farinosa* f sp. *spinaciae*) is a major threat for spinach growers because it directly affects the harvested leaves. In spinach, downy mildew is caused by the oomycete *Peronospora farinosa* f sp. *spinaciae* (formerly known as *P. effusa*). Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f. sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants.

To date 16 pathogenic races of spinach downy mildew (Pfs) have been officially identified and characterized, and many new candidates are observed in the field. The 16 officially recognised races of *Peronospora farinosa* f sp. *spinaciae*, are designated Pfs:1 to Pfs:16 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Ark.) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014, Plantum NL press release, "Denomination of Pfs: 16, a new race of downy mildew in spinach", Mar. 15, 2016). Races 4 to 15 were identified between 1990 and 2014, while only recently another new *Peronospora* isolate has been identified, termed UA201519B, which subsequently has been officially named Pfs:16 by the International Working Group on Peronospora (IWGP) (Plantum NL (Dutch association for breeding, tissue culture, production and trade of seed and young plants) press release, "Denomination of Pfs: 16, a new race of downy mildew in spinach", Mar. 15, 2016. All 16 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

Especially the latest identified *Peronospora* races can break the resistance of many spinach varieties that are currently used commercially worldwide, and they thus pose a serious threat to the productivity of the spinach industry. Therefore, it is crucial to stay at the forefront of developments in this field, as *Peronospora* continuously develops the ability to break the resistances that are present in commercial spinach varieties. For this reason new resistance genes against downy mildew are very valuable assets, and they form an important research focus in breeding and particular in spinach and lettuce breeding. One of the main goals of spinach breeders is to rapidly develop spinach varieties with a resistance to as many *Peronospora* races as possible, including the latest identified races, before these races become wide-spread and pose a threat to the industry.

In commercial spinach varieties resistance against downy mildew is usually caused by so-called R-genes. R-gene mediated resistance is based on the ability of a plant to recognize the invading pathogen. In many cases this recognition occurs after the pathogen has established the first phases of interaction and transferred a so called pathogenicity (or avirulence) factor into the plant cell. These pathogenicity factors interact with host components in order to establish conditions which are favorable for the pathogen to invade the host and thereby cause disease. When a plant is able to recognize the events triggered by the pathogenicity factors a resistance response can be initiated. In many different plant pathogen interaction systems such as the interaction of spinach with different downy mildew strains, the plant initiates these events only after specific recognition of the invading pathogen.

Co-evolution of plant and pathogen has led to an arms race in which a R-gene mediated resistance is sometimes overcome as a consequence of the capability of the pathogen to interact with and modify alternative host targets or the same targets in a different way, such that the recognition is lost and infection can be established successfully resulting in disease. In order to re-establish resistance in a plant, a new R-gene has to be introduced which is able to recognize the mode of action of an alternative pathogenicity factor.

Despite the fact that the durability of R-genes is relatively low, R-genes are in spinach still the predominant form of defense against downy mildew. This is mainly due to the fact that it is the only form of defense that gives absolute resistance. So far plant breeders have been very successful in generating downy mildew resistant spinach varieties by making use of resistance genes residing in the wild germplasm of the crop species. Even though R-genes are extensively used in spinach breeding, until now not much is known of these R-genes. The R-genes present in the current commercial spinach varieties have never been characterized at the molecular level, i.e. their sequence until now was unknown. Also up until now there are no closely linked molecular markers known in the art that separate these R-genes, nor are the molecular characteristics of the genes themselves known in the art. Therefore, the search for new R-genes and R-gene identification is currently based on phenotypic assays in which many accessions are screened for possible variation in their resistance pattern. Subsequently it has to be determined through crossing and selection whether a newly observed resistance is in fact caused by an R-gene.

Citation or identification of any document in this application is not an admission that such document is available as prior art to the present invention.

SUMMARY OF THE INVENTION

Adequately responding to newly emerging downy mildew races is crucial for developing commercially successful spinach varieties. Therefore, it is the object of the invention to provide a new resistance allele conferring resistance to a newly emerged downy mildew isolate and to provide molecular biological tools for identifying this new resistance allele.

In the research leading to the present invention, it was found that different resistance genes that confer resistance to *Peronospora farinosa* f. sp. *spinaciae* in spinach are not separate resistance loci, as had been previously assumed, but that they are different alleles of the same one or two genes. These one or two genes, which are either "alpha-WOLF" type or "beta-WOLF" type genes (together referred to as "the WOLF genes") each encode a protein that belongs to the CC-NB S-LRR family (Coiled Coil—Nucleotide Binding Site—Leucine-Rich Repeat). Depending on the allelic variant (or the allelic variants) that is (are) present in a spinach plant, said plant will produce a variant of the WOLF protein that confers a certain resistance profile to pathogenic races of *Peronospora farinosa* f sp. *spinaciae*. The research leading to the present invention has furthermore elucidated the relationship between the different alleles present in the genome of a spinach plant and the resistance profile of said plant to a number of different pathogenic races of *Peronospora farinosa* f sp. *spinaciae*.

In the context of this invention the term "allele" or "allelic variant" is used to designate a version of the gene that is linked to a specific phenotype, i.e. resistance profile. It was found that a spinach plant may carry one or two WOLF genes. Each of these two WOLF genes encompasses multiple alleles, each allele conferring a particular resistance profile. The beta WOLF gene is located on scaffold12735 (sequence: GenBank: KQ143339.1), at position 213573-221884. In case the spinach plant also carries or only carries the alpha-WOLF gene, the alpha-WOLF gene is located at approximately the same location as where the beta-WOLF gene is located on scaffold12735 in the Viroflay genome assembly.

A screen for novel WOLF-alleles in the spinach germplasm identified a new allele of the alpha-WOLF gene conferring a new and unique resistance profile against several downy mildew races including the recently identified race pfs:16.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "may comprise", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of a plant 16R.58468 that may comprise the alpha-WOLF 8 allele of the invention in its genome were deposited with NCIMB Ltd, Ferguson Building, Craibstone Estate, Bucksburn, Aberdeen AB21 9YA, UK, on Sep. 9 2016, under deposit accession number 42646.

The Deposits with NCIMB Ltd, under deposit accession number 42646 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A genome assembly for spinach variety Viroflay—which is susceptible to all known pathogenic races of *Peronospora* farinosa f. sp. spinaciae—is publicly available (Spinacia oleracea cultivar SynViroflay, whole genome shotgun sequencing project; Bioproject: PRJNA41497; GenBank: AYZV00000000.2; BioSample: SAMN02182572, see also Dohm et al, 2014, Nature 505: 546-549). In this genome assembly for Viroflay, the beta-WOLF gene is located on scaffold12735 (sequence: GenBank: KQ143339.1), at position 213573-221884. The sequence covered by this interval may comprise the entire genomic sequence of the beta-WOLF gene of Viroflay, plus 2000 basepairs sequence upstream from the gene, plus the sequence downstream from the gene, up to the locus of the neighbouring gene that is situated downstream from the WOLF gene. Spinach variety Viroflay only possesses a single WOLF gene, namely a beta-WOLF gene, but most other spinach lines harbor a single alpha-type WOLF gene at the same location in the genome. Other spinach lines harbor two WOLF genes at approximately the same location in the genome. In such cases, the two WOLF genes are positioned adjacent to each other. In most spinach lines that harbor two WOLF genes, one of said WOLF genes belongs to the alpha-type, and the other WOLF gene belongs to the beta-type. In the research leading to the present invention, it was observed that this allelic variation in the WOLF locus is responsible for differences in resistance to pathogenic races of Peronospora farinosa f. sp. spinaciae.

The difference between an allele of an alpha-WOLF gene and an allele of a beta-WOLF gene lies in the presence of specific conserved amino acid motifs in the encoded protein sequence. As mentioned above, all WOLF proteins possess—from N- to C-terminus—the following domains that are generally known in the art: a coiled coil domain (RX-CC-like, cd14798), an NBS domain (also referred to as "NB-ARC domain", pfam00931; van der Biezen & Jones, 1998, Curr. Biol. 8: R226-R228), and leucine-rich repeats (IPR032675) which encompass the LRR domain. In addition, all WOLF proteins comprise in their amino acid sequence the motif "MAEIGYSVC" (SEQ ID NO: 15) at the N-terminus. In addition to this, all alpha-WOLF proteins comprise the motif "KWMCLR" (SEQ ID NO: 16) in their amino acid sequence, whereas all beta-WOLF proteins comprise the motif "HVGCVVDR" (SEQ ID NO: 17) in their amino acid sequence.

The present invention relates to a new Peronospora farinosa f sp. spinaciae resistance conferring allele of the alpha-WOLF gene designated alpha-WOLF 8.

In particular, the invention relates to a Peronospora farinosa f sp. spinaciae resistance conferring allele designated alpha-WOLF 8 wherein the protein encoded by said allele is a CC-NB S-LRR protein that may comprise in its amino acid sequence: a) the motif "MAEIGYSVC" (SEQ ID NO: 15) at its N-terminus; and b) the motif "KWMCLR" (SEQ ID NO: 16); and wherein the LRR domain of the protein has in order of increased preference at least 92%, 93%, 94%, 95%, 96%, 97%, 98%, 99%, 100% sequence similarity to SEQ ID NO:12. Optionally, the alpha WOLF 8 allele may further comprise an additional motif in their amino acid sequence, namely "DQEDEGEDN" (SEQ ID NO: 18).

For the purpose of this invention, the LRR domain of the protein of the alpha-WOLF 8 allele is defined as the amino acid sequence that in order of increased preference has at least 92%, 93%, 94%, 95%, 96%, 97%, 98%, 99%, 100% sequence similarity to SEQ ID NO:12.

The skilled person is familiar with methods for the calculation of sequence similarity. Suitably sequence similarity is calculated using EMBOSS stretcher 6.6.0, the EBLOSUM62 matrix and the resulting "similarity score".

The LRR domain of the alpha-WOLF 8 allele as defined herein can be determined by amplifying and sequencing the genomic DNA encoding for the amino acid sequence of LRR domain using specific primers, and subsequently translating the DNA sequence into an amino acid sequence, thereby applying common sense in choosing the correct reading frame. The skilled person is capable of doing this, using freely available online bioinformatics tools such as can be found here: web.expasy.org/translate/

The genomic sequence of a LRR domain of an alpha-WOLF gene such as alpha-WOLF 8 can be amplified using a primer pair having a forward primer which is a nucleic acid molecule having the sequence of SEQ ID NO:8 and a reverse primer which is a nucleic acid molecule having the sequence of SEQ ID NO:9.

PCR conditions for amplifying the LRR domain-encoding region of an alpha-WOLF gene using primers having SEQ ID NO:8 and SEQ ID NO:9 are, using Platinum Taq enzyme (Thermo Fisher Scientific): 3 minutes at 95° C. (initial denaturing step); 40 amplification cycles, each cycle consisting of: 30 seconds denaturation at 95° C., 30 seconds annealing at 60° C., and 30 seconds extension at 72° C.; 2 minutes at 72° C. (final extension step).

The LRR domain of a beta-WOLF gene, e.g. the null allele as present in variety Viroflay, can be amplified using a forward primer which is a nucleic acid molecule having the sequence of SEQ ID NO:10 and a reverse primer which is a nucleic acid molecule having the sequence of SEQ ID NO:9.

PCR conditions for amplifying the LRR domain-encoding region of a beta-WOLF gene using primers having SEQ ID NO:9 and SEQ ID NO:10 are as follows, using Platinum Taq enzyme (Thermo Fisher Scientific):—3 minutes at 95° C. (initial denaturing step); 40 amplification cycles, each cycle consisting of: 30 seconds denaturation at 95° C., 50 seconds annealing at 58° C. and 50 seconds extension at 72° C.; 2 minutes at 72° C. (final extension step).

Therefore, the invention also relates to a primer pair for amplifying the LRR domain of an alpha-WOLF gene, more in particular for amplifying the LRR domain of an alpha-WOLF 8 allele wherein the forward primer is a nucleic acid molecule having the sequence of SEQ ID NO:8 and the reverse primer which is a nucleic acid molecule having the sequence of SEQ ID NO:9. The primers disclosed herein have been specifically designed for selectively amplifying part of a WOLF gene, and not of any other CC-NB S-LRR protein-encoding genes.

The invention relates to an alpha-WOLF 8 allele which has a genomic sequence that in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

The invention relates to three different splice variants. In one embodiment, the invention relates to an alpha-WOLF 8 allele which has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2. This is the first splice variant of the alpha-WOLF 8 allele.

In a further embodiment the alpha-WOLF 8 allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3. This is the second splice variant.

In another embodiment the alpha-WOLF 8 allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4. This is the third splice variant.

In a further aspect of the invention the alpha-WOLF 8 allele encodes for a protein having an amino acid sequence which in order of increased preference has at least 92%, 93%, 94%, 95%, 96%, 97%, 98%, 99%, 100% sequence similarity to SEQ ID NO:5.

In another embodiment the alpha-WOLF 8 allele encodes for a protein having an amino acid sequence which in order of increased preference has at least 92%, 93%, 94%, 95%, 96%, 97%, 98%, 99%, 100% sequence similarity to SEQ ID NO:6.

In yet a further embodiment the alpha-WOLF 8 allele encodes for a protein having an amino acid sequence which in order of increased preference has at least 92%, 93%, 94%, 95%, 96%, 97%, 98%, 99%, 100% sequence similarity to SEQ ID NO:7.

The alpha-WOLF 8 allele when homozygously present in a spinach plant confers complete resistance to the officially recognized *Peronospora farinosa* f. Sp. *spinacea* races pfs: 1, pfs:2, pfs:6, pfs:8 and pfs:15, and confers intermediate resistance to pfs:5, pfs:10 and pfs:16, and does not confer resistance to downy mildew races pfs:3, pfs:4, pfs:7, pfs:9, pfs:11, pfs:12, pfs:13 and pfs:14 (See Table 1). As indicated in Table 1, a spinach plant heterozygous for the alpha-WOLF 8 allele and not carrying any other resistance conferring allele will be susceptible for downy mildew races Pfs:5, Pfs:10, and Pfs:16.

The resistance of a spinach plant against one or more races of *Peronospora farinosa* f. sp. *Spinaciae* can be determined using a seedling test. Herein, a seedling test is defined as a test wherein spinach plants are planted in trays containing growth medium, optionally fertilized twice a week after seedling emergence. Plants were inoculated at the first true leaf stage with a sporangial suspension having a concentration of approximately $2.5 \times 10^5$/ml of one of the pathogenic races of *Peronospora farinosa* f sp. *spinaciae* or isolates to be tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction. Preferably, 30 plants per race are tested.

As used herein, a plant is completely resistant against a *Peronospora farinosa* f sp. *spinaciae* race when a plant shows no symptoms in the seedling test described herein.

As used herein, a plant is intermediately resistant against a *Peronospora farinosa* f. sp. *spinaciae* race when a plant shows only symptoms of chlorosis, or sporulation occurring only on the tips of the cotyledons in the seedling test described herein.

As used herein, a plant is susceptible to an isolate of a *Peronospora farinosa* f. sp. *spinaciae* race when a plant shows more than only symptoms of chlorosis, or when sporulation occurs on area larger than only the tips of the cotyledons in the seedling test described herein.

Another aspect of the invention relates to a spinach plant, which may comprise the alpha-WOLF 8 allele of invention, of which a representative sample of seed was deposited with the NCIMB under NCIMB accession number 42646.

In a further embodiment the plant of the invention which may comprise the alpha-WOLF 8 allele is an agronomically elite spinach plant. In the context of this invention an agronomically elite spinach plant is a plant having a genotype that results into an accumulation of distinguishable and desirable agronomic traits which allow a producer to harvest a product of commercial significance, preferably the agronomically elite spinach plant which may comprise the alpha-WOLF 8 allele is a plant of an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

A plant carrying the alpha-WOLF 8 allele in heterozygous form may further comprise a beta-WOLF 0 allele as e.g. present in variety Viroflay wherein the beta-WOLF 0 allele does not confer any resistance to downy mildew. However, a plant heterozygous for the alpha-WOLF 8 allele may further comprise an allele of the alpha/beta-WOLF gene that does provide resistance to downy mildew. Preferably, such an allele would complement the alpha-WOLF 8 allele such that the spinach plant will be at least intermediately resistant to one or more other races to which the alpha-WOLF 8 allele does not provide resistance. Most preferably the other allele of the alpha/beta-WOLF gene complements the alpha-WOLF 8 allele such that the plant is resistant to *Peronospora farinosa* f. sp. *spinaciae* races Pfs:1 to Pfs:16. In one embodiment such a plant is an agronomically elite plant.

Alternatively, the resistance profile of a plant carrying the alpha-WOLF 8 allele is complemented by a resistance conferring allele of a totally different gene. Examples of such genes are e.g. DMR1 as described in U.S. Pat. No. 8,354,570 and DMR6 as described in U.S. Pat. No. 9,121,029.

The invention thus relates to a spinach plant carrying the alpha-WOLF 8 allele and further which may comprise a genetic determinant resulting in resistance against *Peronospora farinosa* f Sp. *spinacea* races pfs:1 to pfs:16. The genetic determinant can be another resistance conferring alpha/beta-WOLF allele or a resistance conferring allele of a totally different gene.

The invention further relates to propagation material which may comprise the alpha-WOLF 8 allele. In one embodiment, the propagation material is suitable for sexual reproduction. Such propagation material may comprise for example a microspore, pollen, ovary, ovule, embryo sac and egg cell. In another embodiment, the propagation material is suitable for vegetative reproduction. Such propagation material may comprise for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention furthermore relates to a cell of a spinach plant which may comprise the alpha-WOLF 8 allele. Such a cell may be either in isolated form or may be part of the complete plant or parts thereof and then still constitutes a cell of the invention because such a cell harbors the alpha- WOLF 8 allele that confers resistance to downy mildew. Each cell of a plant of the invention carries the genetic information that confers resistance to *Peronospora farinosa* f sp. *spinaciae*. Such a cell of the invention may also be a regenerable cell that can be used to regenerate a new plant which may comprise the allele of the invention.

Yet another aspect of the invention relates to a method for making a hybrid spinach seed which may comprise crossing a first parent spinach plant with a second parent spinach plant and harvesting the resultant hybrid spinach seed, wherein said first and/or second parent spinach plant may comprise the alpha-WOLF 8 allele. In particular embodiment, the first and/or second parent plant is a plant of an inbred line as defined herein.

The invention further relates hybrid spinach plant grown from seed produced by crossing a first parent spinach plant with a second parent spinach plant and harvesting the resultant hybrid spinach seed, wherein said first and/or second parent spinach plant may comprise the alpha-WOLF 8 allele.

Another aspect of the invention relates to a method for identifying or selecting a spinach plant carrying the alpha-WOLF 8 allele, which may comprise determining the presence of a genomic nucleotide sequence or a part thereof in the genome of a plant, wherein said sequence has in order of increased preference 92%, 93%, 94%, 95%, 96%, 97%, 98%, 99%, 100% sequence similarity to SEQ ID NO:1.

The invention further relates a method for identifying or selecting a spinach plant carrying the alpha-WOLF 8 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to SEQ ID NO:2.

The invention further relates a method for identifying or selecting a spinach plant carrying the alpha-WOLF 8 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to SEQ ID NO:3.

The invention further relates a method for identifying or selecting a spinach plant carrying the alpha-WOLF 8 allele, which may comprise determining the presence of a coding sequence or a part thereof in the genome of a plant, wherein said sequence has in order of increased preference 92%, 93%, 94%, 95%, 96%, 97%, 98%, 99%, 100% sequence similarity to SEQ ID NO:4.

Determining the genomic DNA or coding DNA sequence of at least part of a WOLF gene in the genome of a spinach plant may be performed using any suitable molecular biological method known in the art, including but not limited to (genomic) PCR amplification followed by Sanger sequencing, whole-genome-sequencing, transcriptome sequencing, sequence-specific target capture followed by next-generation sequencing (using, for example, the xGen® target capture system of Integrated DNA Technologies), specific amplification of LRR-domain-which may comprise gene sequences (using, for example, the RenSeq methodology, as described in U.S. patent application Ser. No. 14/627,116, and in Jupe et al., 2013, *Plant J.* 76: 530-544) followed by sequencing, etcetera.

In another embodiment the invention relates to a method for identifying or selecting a plant carrying the alpha-WOLF 8 allele which may comprise determining the DNA sequence coding for the LRR domain as defined herein.

In a further embodiment of the method the LRR domain of the alpha-WOLF 8 allele is determined by using a primer pair to amplify the genomic DNA region of the LRR domain. The forward primer is preferably a nucleic acid molecule having the sequence of SEQ ID NO:8 and the reverse primer is preferably a nucleic acid molecule having the sequence of SEQ ID NO:9.

Another aspect of the invention relates to a method for producing a spinach plant which may comprise resistance to *Peronospora farinosa* f sp. *spinaciae* which may comprise: (a) crossing a plant which may comprise the alpha-WOLF 8 allele, with another plant; (b) optionally performing one or more rounds of selfing and/or crossing; (c) optionally selecting after each round of selfing or crossing for a plant that may comprise the alpha-WOLF 8 allele.

Selecting a plant which may comprise the alpha-WOLF 8 allele can be done genotypically by determining the presence of the genomic DNA sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

In another embodiment, selecting a plant which may comprise the alpha-WOLF 8 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

In another embodiment, selecting a plant which may comprise the alpha-WOLF 8 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

In yet another embodiment, selecting a plant which may comprise the alpha-WOLF 8 allele can be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4.

Alternatively, the presence of the alpha-WOLF 8 allele can be determined phenotypically by assaying a plant in a disease test, for example the test as described herein, and identifying a plant carrying the alpha-WOLF 8 allele based on the resistance pattern as described herein and indicated in Table 1.

The invention further relates to the use of a spinach plant carrying the alpha-WOLF 8 allele in breeding to confer resistance against *Peronospora farinosa* f. sp. *spinaciae*.

The invention also relates to a breeding method for the development of spinach plants carrying the alpha-WOLF 8 allele of the invention wherein germplasm which may comprise said allele is used. Seed capable of growing into a plant which may comprise the allele of the invention and being representative for the germplasm was deposited with the NCIMB under deposit number NCIMB 42646.

In another aspect, the invention relates to a method for the production of a spinach plant which may comprise the alpha-WOLF 8 allele, which method may comprise: (a) crossing a plant which may comprise the allele with another plant; (b) optionally selecting for plants which may comprise said allele in the F1; (c) optionally backcrossing the resulting F1 with the preferred parent and selecting for plants that have the said allele in the BC1F1; (d) optionally performing one or more additional rounds of selfing, crossing, and/or backcrossing, and subsequently selecting for a plant which may comprise the said allele or shows the resistance profile corresponding to said allele. The invention also encompasses a spinach plant produced by this method.

The invention also relates to a harvested leaf of a spinach plant of the invention, to a food product which may comprise a harvested leaf of a spinach plant of the invention, either in natural or in processed form.

Spinach leaves are sold in packaged form, including without limitation as pre-packaged spinach leaves or as processed in a salad which may comprise said leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves of spinach plants derived from the invention.

The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

The invention also relates to the use of a spinach plant, of which representative seed was deposited with the NCIMB under accession number NCIMB 42646, in the production of a spinach plant which may comprise the alpha-WOLF 8 allele.

In a further embodiment the said spinach plant is a hybrid, doubled haploid, or inbred spinach plant.

Another aspect of the invention is the use of a cell which may comprise the alpha-WOLF 8 allele for the production of a spinach plant showing resistance to *Peronospora farinosa* f. sp. *spinaciae*.

The invention also relates to the use of a tissue culture which may comprise the alpha-WOLF 8 allele for the production of a spinach plant showing resistance to *Peronospora farinosa* f. sp. *spinaciae*.

TABLE 1

Resistance Information.
Alpha-WOLF 8 resistance profile

| *Peronospora farinosa* f. sp. *Spinaciae* race | Resistance score |
|---|---|
| Pfs: 1 | − |
| Pfs: 2 | − |
| Pfs: 3 | + |
| Pfs: 4 | + |
| Pfs: 5 | (−)* |
| Pfs: 6 | − |
| Pfs: 7 | + |
| Pfs: 8 | − |
| Pfs: 9 | + |
| Pfs: 10 | (−)* |
| Pfs: 11 | + |
| Pfs: 12 | + |
| Pfs: 13 | + |
| Pfs: 14 | + |
| Pfs: 15 | − |
| Pfs: 16 | (−)* |

Resistance profile conferred by the Alpha-WOLF 8 allele. A "−" means complete resistance against a particular downy mildew race; "(−)" means intermediate resistance against a particular downy mildew race; "+" means that the allele confers no resistance and would cause a plant only carrying the Alpha-WOLF 8 allele to be fully susceptible for that particular downy mildew race.
*The intermediate resistances against Pfs: 5, Pfs: 10 and Pfs: 16 conferred by the alpha-WOLF 8 allele are only observed in homozygous state. A plant carrying the allele in heterozygous state and not carrying any other resistance conferring allele (i.e. carrying the beta-WOLF zero allele) would be susceptibile for Pfs: 5, Pfs: 10, and Pfs: 16.

TABLE 2

| Sequence information. | |
|---|---|
| SEQ ID NO: 1:<br>Genomic<br>sequence of<br>alpha-WOLF 8 | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA |

TABLE 2-continued

Sequence information.

```
AGTAAGTGGCGGTCATTTGAAATGAGTGAGTTGGCCAAAAT
TGGCAATGGGATAATAAGATTTTGCCGATATTAAAGCTCA
GTTACCATAATCTTATACCCTCGTTGAAGAGTTGCTTCAGTT
ATTGTGCAGTGTTTCCCAAGGATCATGAAATAAAGAAGGAG
ATGTTGATTGATCTTTGGATAGCACAAGGATACGTTGTGGCA
CTTGATGGAGGTCAAAGTATAGAAGATGCTGCCGAAGAACA
TTTTGTAATTTTGTTACGGAGATGTTTCTTTCAAGATGTAAA
GAAGGATGAATATGGTGATGTTGATTCTGTTAAAATCCACG
ACTTGATGCACGATGTCGCCCAAGAAGTGGGGAGGGAGGAA
ATATGTAGTGAATGATAATACAAAGAACTTGGGTGATAA
AATCCGTCATGTACATGGTGATGTCAATAGATATGCACAAA
GAGTCTCTCTGTGTAGCCATAGCCATAAGATTCGTTCGTATA
TTGGTGGTGATTGTGAAAAACGTTGTGTGGATACACTAATAG
ACAAGTGGATGTGTCTTAGGATGTTGGACTTGTCATGGTCGG
ATGTTAAAAATTTGCCTAATTCAATAGGTAAATTGTTGCACT
TGAGGTATCTTAACCTGTCAGATAATAGAAATCTAAAGATA
CTTCCTGATGCAATTACAAGACTGCATAATTTGCAGACACTG
CTTTTAAAAGATTGCAGAAGTTTAAAGGAGTTGCCAAAAGA
TTTTTGCAAATTGGTCAAACTGAGACACTTGGATTTATGGGG
TTGTGATGATTTGATTGGTATGCCATTTGGAATGGATAAGCT
AACTAGTCTTAGAATACTACCAAACATTGTGGTGGGTAGGA
AGGAACAAAGTGTTGATGATGAGCTGAAAGCCCTTAAAGGC
CTCACCGAGATAAAAGGCGACATTGATATCAAATCTGTGA
AAATTATAGAATAGTTGAAGGCATGAATGACACAGGAGGAG
CTGGGTATTTGAAGAGCATGAAACATCTCAGGGAGATTGGT
ATTACATTTGATGGTGGATGTGTTAACCCTGAAGCTGTGTTG
GCAACCCTAGAGCCACCTTCAAATATCAAGAGCTTATCTATA
CATCGTTTTGATGGTAAAACACTTCCAGTATGGGGAAGAGC
AGAGATTAATTGGGCAATCTCCCTCTCACATCTTGTCGACAT
CCAGCTTTGGCATTGTCGTAATTTGCAGGAGATGCCAGTGCT
GAGTAAACTGCCTCATTTGAAATCACTGGAACTTTATAATTT
GATTAGTTTAGAGTACATGGAGAGCACAAGCAGAAGCAGTA
GCAGTGACACAGAAGCAGCAACACCAGAATTACCAACATTC
TTCCCTTCCCTTGAAAAACTTACACTTTGGGGTCTGGAAAAG
TTGAAGGGTTTGGGGAACAGGAGATCGAGTAGTTTTCCCCG
CCTCTCTGAATTGAAAATCATGGAATGCCCAGATCTAACGTG
GTTTCCTCCCTGTCCAAGCCTTGAAAAACTTACACTTTGGCG
TCTGGACAAGTTGAAGGGTTTTGGGAACCGGAGATCGAGTA
CTTTTCCCCGCCTCTCTGAATTGGAAATCAAGAAATGCCCAG
ATCTAACGTCATTTCCTTCTTGTCCAAGCCTTGAGAAGTTGG
AATTGAAAGAAAGCAATGAAGCATTGCAAATAATAGTAAAA
ATAACAACAAGAGGTAAAGAAAAAGAAGAGAACAATAATG
CTGGTGTTAGAAATTCACAAGATGATGACAAAGTCAAATTA
CGGAAGATGGTGATAGACAATCTGGGTTATCTCAAATCACT
GCCCACAAATTGTCTTACTCACCTCGACCTTACAATAAGTGA
TTCCAAGGAGGGGAGGGTGAATGGGAAGTTGGGGATGCAT
TTCAGAAGTGTGTATCTTCTTTGAGAAGCCTCACCATAATCG
GAAATCACGGAATAAATAAAGTGAAGAGACTGTCTGGAAGA
ACAGGGTTGGAGCATTTCACTCTGTTGGAATCACTCAAACTT
TCAGATATAGAAGACCAGGAAGATGAGGGCGAAGACAACA
TCATATTCTGGAAATCCTTTCCTCAAAACCTCCGCAGTTTGA
GAATTAAAGACTCTGACAAAATGACAAGTTTGCCCATGGGG
ATGCAGTACTTAACCTCCCTCCAAACCCTCTATCTACACCAT
TGTTATGAATTGAATTCCCTTCCAGAATGGATAAGCAGCTTA
TCATCTCTTCAATACCTGCGCATATACTACTGTCCAGCCCTG
AAATCACTACCAGAAGCAATGCGGAACCTCACCTCCCTTCA
GACACTTGGGATATCGGATTGTCCAGACCTAGTTAAAAGAT
GCAGAAAACCCAACGGCAAGGACTATCCCAAAATTCAACAC
ATCCCCTATTGGAGTATAGAACATCAGGTTATAACTAGCTTG
TAACTAACTTGTAACTACCTAGTATAAATACAGTAGTTTGTA
CTATTTTACATTCAATTACACAATTAATAAAATGTAGACTCT
CACTCTCTCTCTAAGCCACGAGCTCCAAGCTCGTCAATGG
CTTCCCTTCTCTGTTCTTGCTTTCTTCTTTCCTCTTCAATTCAC
AAATTCAACATGGTATCAGAGCGGGACGATCCTTGCTCTTCA
CTTCCGCACAAAATTTCGTTCAATTCAACCCATCAAATTTTT
TTTTTCCCCCAAATTTTCTCGAATTCGGTCAAAATTCGACGA
ATTAGGGATTCAATTTACCCTGATTTCTTCTGATTCCATTCAA
TGATTGTTCATTTCGAATCTTGAATCAAATAATTGTTGATTCT
GGATTCCCCAAATTCTAGGGTTCTTGAAGGATTTACAAGAAT
CTGGCATTGCTGATAGATTCTTGAAGCAATTTGCGTCTCCGT
GTTCCTCGGTGGTCTTGAGTTTGTTTCCGTATTCGCTGCTCTC
ATCTTTACTGGGGATTGTGGTCTGATTTCTTGGCTTCCTCTGT
CGATGATGTGATTGGTAATACTTAAAACCCTCTCTCTTT
CCGAAATTATTGATGCTGGTCGTCATTTTTTTTTTTGGAATC
ATCTCAGTTTATCGCCGCAATTTGAGTTGTTGTTGGGTAATT
GTTGTTGCTGCCGATGATGTTTTGTGAATTTGAGAATTGTTA
GAATGATTCTTGTTCAATCAATTTGGTTCTCATACTCTAATG
GAAGCCTGTTTTGGAGCGACGAATTATGCAATTCTGAGATTT
```

TABLE 2-continued

Sequence information.

```
CTTTTGATCCTTATTTCTTTTCTTCACTTGAATTTCTGGTGTTT
GTGAGTAATTCTTGGTTAATGTTTGATCTGGGTAGTTCTTGG
GTTTACTGAAGACGTTTCTTGAAGGTTTTGACAGAAAAGCTG
AGGTTTAATTCCAAAATTCTTCTGTCCAATTACATTTTTATTG
TTGATGGTTCTTATGTGAGAACTAGACTGAGTTTTTTTTATG
AAATTGTTTCGACCTTCAGATGGATTCGAGAGATTTGAGTTC
ATTTTCTTTGATGAATGTGTTAGAAAAGGTTTTGGTGCAGTG
ACCATTTTAAACCAAATAGAGTTACATAAATATTGGGATTCT
TTTCTGGGAATGTAGTTAGGAGTTGAAATCTTTTGGAGCTGC
TTTACCATAAAACCCAGCCTCAGAGTCTGTTAACCAGTTAGG
ACCGTGTAAACATGATCCCAGGCTGCATTTGCGTTATCAGAT
TTGATTCAGTTTTGGAATTGTGGATTTTGAGGGTTTAAAAGC
TTACAGTTGCTCCTGGAGAATGGTGTGAGCAATATAGGAATT
CAGCACTAGTATTGCAGAAAATGAAGCTTGGTTGTTGATTGT
TGGCATGTTTTGTTGCCATTGTTTTGGGTTGATGTTTTCCTTT
TCTTTTGAATGTTGGCACGATTCAACATTTCTTTCCTGCAACA
GATTTGGAGTTCAGTACCTGTATAATCAGGTCAATTTTGTTC
ATTTTTCCCAGCAACAGATCTGGAGAATCAGAACCTGTAAA
ANNNNNNNNNNNNNNNNNNNNNNNNNNNNNNNNNNNNNN
NNNNNNNNNNNNNNNNNNNNNNACCCAAAGAGGTCAGTTT
TCATTGATCCATTGTGATCATTCTTTTGATGAGACCCATTGA
GGCTCATTTCTTCAAGGCAATATTGGAAGTTGTAGATTGATA
TGAGCAGTTGGTACAACAGCAACAAAAGTGGCCAGCATCTA
TGCTTGTTCATGAGGAGTTCTTGGTGCAGAGTTAATGAAGAG
TCTGTTTTGAAGCTTTCAAACTGAAGATGTTTATCACCATCT
CCAGTTTGAGGGGGGGTATTGGAGTATAGAACATCAGGTTA
TAACTAGCTTGTAACTAACTTGTAACTACCTAGTATAAATAC
AGTAGTTTGTACNNNNNNNNNNNNNNNNNNNNNNNNNNNN
NNNNNNNNNNNNNNNNNNNNCCACGAGCTCCAAGCTCG
TCAATGGCTTCCCTTCTCTGTTCTTGCTTTCTTCTTTCCTCTTC
AATTCACAAATTCAACATCCCCAAAATTGTAAGTCATTGCAG
AAAGTAATTTATTCATTTATATTTATTTTATGCTTAGAATGAT
ATACGCAGTCGTCCTTTGGTTTCAAATCTTGAATTTGGTTTTT
GTTTTCTTTCTTTGTTTCTTTATTCAACACCAGCCCATTTATG
ATTGATTCATTAAAAAAAGGATGGAGTTTTATGGATTTGAAG
AAGACAACGAATTGAGATTCCTGGGGTTTTCTTTTTGTTGGG
GTTGGATTTCATGTATATGTTGCTGATTAAATACGAGACTGA
TGATGATGATGTGTTTATGGGTTTTAAATCAGATTAAATATA
TGGGAAATGCAAGTTAATTTGGGATGCACATAAGGTGTTTG
CTGAAATGTCTATGAGAAATGTTGTTTCTTGGACTTAGAATG
ATATACACTGTCGTCCTTTGGTTTCCAATCTTACATTTGGTTT
GTGTTTTCTTAGTTTGTTTCTTTAATCAACACCAACCCGTTTT
TTTTAAACTACCTGCAACTACTAATTTACGTTTACCCTGTATC
TCAGGTACTAAATGAATATTGGTGATTTTCAGTTACTCAACA
CTAGCTTGATCCTGAACGCACCCAACCTTCAGGTTAGAATCC
GGCTTACTCATCCTTTTGTCCAGTTTTCAAGTAATTGTTTTGG
CAGGATCAATTCTCTAATTGTTGTACACCGTATATTGCAATT
TATAGTGACTACAGTTAATGAATGTTTACAAAAAATTAGTCA
TGTAAAAACTTCTTCTCTGTCCATTACATAAACTCTTTTTCTC
TTTCTAACTTATCATGTTCATGTCTAAACAATTAAACATGCT
CACATCAATGTTCATTTAAGCTAACTTACTTCTGTAAGAGAG
CGAGCTAGTTAAAAACTCCTTTAACTTTCTGTTTTATACTCA
GGACATGGATTGATGCAAGCATGAAGAACTTCGGGAATTTG
CTAAAACTCTACCAAAGCGATGAGAGTTTGGACTTTATTTCA
CTTGAAGTCAGGGACTGTCAACAAAGCCACAGTGTGCATGT
TGGCTGTTTCACTTGGACGATAAAAAGGTTTATTTAATTGTT
TTCCTAAGTGTATTTGGCTTACAAGCTTTTACTTTTCACTTGA
AAGGGTTTTTCTTGTTTTAAGCTTTTCGAATTAGAGTTTTCGG
TTGAAGTAAGAGTAGTCGTATTAGTCTTTTACCTAAGGAAGA
CTCTTTTTTGTAATTTTCAGACTATGCAATTCAAGTTTTCGAG
TGTTTTCTTGCTTGTGTGATTGTGAGTTGGTGAATTCGTCTTT
CATACATTTTGAGATTATCAGAAGCTTTATGCTCCACCGGTA
GTCTAGTACCTTTTCTGTTACTGTGCAGGGAAGTAATCTGGT
ACCTTCTATATATATGGAAAAACATACATTATACATTATGCA
AAATTCTTACAGGTTAGTTACTTCCTGGAACTTCATTTACAC
TTAGTTTTTTTGTTCCATTCCCTCGGAATCAAGTCATTCCCT
CTGAGAAATATGTAATGAACTTCTGTATGTTGCTGTTTGGTT
CCTGTTTTAATCTTCAATTTCTTGTATAGTTACAGCTGCATT
TACAATGAAGTTTAAGCAGACACTCTCTTTATATAGTGCCTC
TTTCTGGAGCACCGTAGAGCTGTCTGTGGTTGATCACCATCT
GCTGCCGAGAGATTCAGCAATCGCGTGTTTGATCAGGTAAA
AGTTTTTATGTCAATGTGTTTTTTTTCCGTTTGATCAATTTA
TGTCTGTATTCAGATTCTTATCTTCTTACAGTAGCATAACAC
ATTGTTTCTTTCATTTATGTAAACTGTTTCAAGATTACAGAG
ATGTATGCTTCAGTCGACATTGATGATAACTTAAGATGGCAT
TCCTACAACAGTTGCAGGCGCATTCTAACTCCGGCAATTCTA
GTTAGGCAAGAGGAGCATTGCCAATACCTGCCACCTCTGGG
ATTTACTATACCAGGGTTGAAGTTTATGGAAGACACCAGCTA
```

TABLE 2-continued

Sequence information.

|  |  |
|---|---|
|  | TGCACAAGCCTTCAAGGGGTCATCCTACATAACAAGTTGAA<br>CCAACCAATTGCTTGTTGGTTCAGTGGTAATTGAAGCTGAAT<br>TTGGTAGGGATGGCCCGTGTTCGATCCCCACAACAACAATTG<br>GGAGGGGACTGGAACCTATCCACACAGAACTCGCCCTGAAT<br>CCGGATTAGCCCTAAGGGTGAACGGGGTGCTAACACCAAAA<br>AAAAAAACATAACAAGTTGAACCAAACATACTTTGTTTGAA<br>TTGAAGATTTAGTGATTTCATTTGATCGATTGAGATGTCTTA<br>TTATAAGCGTATATGCTCTTGGATTTGGCCACTTAGGTGTTG<br>TTTGACAATTGGACATTAACTCGCTTTTATATTTTCTTTTCTC<br>TTAGGAAAGGTGATCCTGAGAATTTATATTGGAACACTTTTT<br>TTTTCTCACTAGCTTTAAAAAAGTGTTCTGTGTTACCTGCAAT<br>TCAATTTGATTATTTTTCACATAGTTTTACCTGAAAAAGTGTT<br>ACCTGAAAAAGTGTTACCTGAAAATCAACTGACATAAGTTTT<br>TGTTTGGATCCAATTAAGGACACTAGATAAATCGGAATAAA<br>TAATCAACCAATTAAGTACTTCATAATTAAATATGAAGTGTA<br>TTATTATCTTATGCTTGTGACATTGAAGGATGTTATGATATTT<br>TAACTCAATACCTTGCAAATATACTGG |
| SEQ ID NO: 2:<br>cds alpha-<br>WOLF 8 | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTAGTGAATGATAATACAAAGAACTTGGGTGATAA<br>AATCCGTCATGTACATGGTGATGTCAATAGATATGCACAAA<br>GAGTCTCTCTGTGTAGCCATAGCCATAAGATTCGTTCGTATA<br>TTGGTGGTGATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCCATTTGGAATGGATAAGCT<br>AACTAGTCTTAGAATACTACCAAACATTGTGGTGGGTAGGA<br>AGGAACAAAGTGTTGATGATGAGCTGAAAGCCCTTAAAGGC<br>CTCACCGAGATAAAAGGCGACATTGATATCAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA<br>CATCGTTTTGATGGTAAAACACTTCCAGTATGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT<br>GATTAGTTTAGAGTACATGGAGAGCACAAGCAGAAGCAGTA |

TABLE 2-continued

Sequence information.

|  |  |
|---|---|
|  | GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG<br>CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAAGACAACA<br>TCATATTCTGGAAATCCTTTCCTCAAAACCTCCGCAGTTTGA<br>GAATTAAAGACTCTGACAAAATGACAAGTTTGCCCATGGGG<br>ATGCAGTACTTAACCTCCCTCCAAACCCTCTATCTACACCAT<br>TGTTATGAATTGAATTCCCTTCCAGAATGGATAAGCAGCTTA<br>TCATCTCTTCAATACCTGCGCATATACTACTGTCCAGCCCTG<br>AAATCACTACCAGAAGCAATGCGGAACCTCACCTCCCTTCA<br>GACACTTGGGATATCGGATTGTCCAGACCTAGTTAAAAGAT<br>GCAGAAAACCCAACGGCAAGGACTATCCCAAAATTCAACAC<br>ATCCCCTATTGGAGTATAGAACATCAGGTTATAACTAGCTTG<br>TAA |
| SEQ ID NO: 3:<br>cds of alpha-<br>WOLF 8<br>(isoform 1) | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAATTGAGTTCCATGATT<br>TGAGGTATTGGGTTTGTGTCTCTGATCAAGATGGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTAATGATAATACAAAGAACTTGGGTGATAA<br>AATCCGTCATGTACATGGTGATGTCAATAGATATGCACAAA<br>GAGTCTCTCTGTGTAGCCATAGCCATAAGATTCGTTCGTATA<br>TTGGTGGTGATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCCATTTGGAATGGATAAGCT<br>AACTAGTCTTAGAATACTACCAAACATTGTGGTGGGTAGGA |

TABLE 2-continued

Sequence information.

|  |  |
|---|---|
| | AGGAACAAAGTGTTGATGATGAGCTGAAAGCCCTTAAAGGC<br>CTCACCGAGATAAAAGGCGACATTGATATCAAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA<br>CATCGTTTTGATGGTAAAACACTTCCAGTATGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT<br>GATTAGTTTAGAGTACATGGAGAGCACAAGCAGAAGCAGTA<br>GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG<br>CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAAGACAACA<br>TCATATTCTGGAAATCCTTTCCTCAAAACCTCCGCAGTTTGA<br>GAATTAAAGACTCTGACAAAATGACAAGTTTGCCCATGGGG<br>ATGCAGTACTTAACCTCCCTCCAAACCCTCTATCTACACCAT<br>TGTTATGAATTGAATTCCCTTCCAGAATGGATAAGCAGCTTA<br>TCATCTCTTCAATACCTGCGCATATACTACTGTCCAGCCCTG<br>AAATCACTACCAGAAGCAATGCGGAACCTCACCTCCCTTCA<br>GACACTTGGGATATCGGATTGTCCAGACCTAGTTAAAAGAT<br>GCAGAAAACCCAACGGCAAGGACTATCCCAAAATTCAACAC<br>ATCCCCTATTGGAGTATAGAACATCAGGTACTAAATGAATAT<br>TGGTGA |
| SEQ ID NO: 4:<br>cds of alpha-<br>WOLF 8<br>(isoform 2) | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGAT<br>TGAGGTATTGGGTTTGTGTCTCTGATCAAGATGGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATCGTTGTGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTGAATGATAATACAAAGAACTTGGGTGATAA |

TABLE 2-continued

Sequence information.

```
AATCCGTCATGTACATGGTGATGTCAATAGATATGCACAAA
GAGTCTCTCTGTGTAGCCATAGCCATAAGATTCGTTCGTATA
TTGGTGGTGATTGTGAAAAACGTTGTGTGGATACACTAATAG
ACAAGTGGATGTGTCTTAGGATGTTGGACTTGTCATGGTCGG
ATGTTAAAAATTTGCCTAATTCAATAGGTAAATTGTTGCACT
TGAGGTATCTTAACCTGTCAGATAATAGAAATCTAAAGATA
CTTCCTGATGCAATTACAAGACTGCATAATTTGCAGACACTG
CTTTTAAAAGATTGCAGAAGTTTAAAGGAGTTGCCAAAAGA
TTTTTGCAAATTGGTCAAACTGAGACACTTGGATTTATGGGG
TTGTGATGATTTGATTGGTATGCCATTTGGAATGGATAAGCT
AACTAGTCTTAGAATACTACCAAACATTGTGGTGGGTAGGA
AGGAACAAAGTGTTGATGATGAGCTGAAAGCCCTTAAAGGC
CTCACCGAGATAAAAGGCGACATTGATATCAAAATCTGTGA
AAATTATAGAATAGTTGAAGGCATGAATGACACAGGAGGAG
CTGGGTATTTGAAGAGCATGAAACATCTCAGGGAGATTGGT
ATTACATTTGATGGTGGATGTGTTAACCCTGAAGCTGTGTTG
GCAACCCTAGAGCCACCTTCAAATATCAAGAGCTTATCTATA
CATCGTTTTGATGGTAAAACACTTCCAGTATGGGGAAGAGC
AGAGATTAATTGGGCAATCTCCCTCTCACATCTTGTCGACAT
CCAGCTTTGGCATTGTCGTAATTTGCAGGAGATGCCAGTGCT
GAGTAAACTGCCTCATTTGAAATCACTGGAACTTTATAATTT
GATTAGTTTAGAGTACATGGAGAGCACAAGCAGAAGCAGTA
GCAGTGACACAGAAGCAGCAACACCAGAATTACCAACATTC
TTCCCTTCCCTTGAAAAACTTACACTTTGGGGTCTGGAAAAG
TTGAAGGGTTTGGGGAACAGGAGATCGAGTAGTTTTCCCCG
CCTCTCTGAATTGAAAATCATGGAATGCCCAGATCTAACGTG
GTTTCCTCCCTGTCCAAGCCTTGAAAAACTTACACTTTGGCG
TCTGGACAAGTTGAAGGGTTTGGGAACCGGAGATCGAGTA
CTTTTCCCCGCCTCTCTGAATTGGAAATCAAGAAATGCCCAG
ATCTAACGTCATTTCCTTCTTGTCCAAGCCTTGAGAAGTTGG
AATTGAAAGAAAGCAATGAAGCATTGCAAATAATAGTAAAA
ATAACAACAAGAGGTAAAGAAAAAGAAGAGAACAATAATG
CTGGTGTTAGAAATTCACAAGATGATGACAAAGTCAAATTA
CGGAAGATGGTGATAGACAATCTGGGTTATCTCAAATCACT
GCCCACAAATTGTCTTACTCACCTCGACCTTACAATAAGTGA
TTCCAAGGAGGGGGAGGGTGAATGGAAGTTGGGGATGCAT
TTCAGAAGTGTGTATCTTCTTTGAGAAGCCTCACCATAATCG
GAAATCACGGAATAAATAAAGTGAAGAGACTGTCTGGAAGA
ACAGGGTTGGAGCATTTCACTCTGTTGGAATCACTCAAACTT
TCAGATATAGAAGACCAGGAAGATGAGGGCGAAGACAACA
TCATATTCTGGAAATCCTTTCCTCAAAACCTCCGCAGTTTGA
GAATTAAAGACTCTGACAAAATGACAAGTTTGCCCATGGGG
ATGCAGTACTTAACCTCCCTCCAAACCCTCTATCTACACCAT
TGTTATGAATTGAATTCCCTTCCAGAATGGATAAGCAGCTTA
TCATCTCTTCAATACCTGCGCATATACTACTGTCCAGCCCTG
AAATCACTACCAGAAGCAATGCGGAACCTCACCTCCCTTCA
GACACTTGGGATATCGGATTGTCCAGACCTAGTTAAAAGAT
GCAGAAAACCCAACGGCAAGGACTATCCCAAAATTCAACAC
ATCCCCTATTGGAGTATAGAACATCAGTTACTCAACACTAGC
TTGATCCTGAACGCACCCAACCTTCAGGACATGGATTGA
```

SEQ ID NO: 5:
protein
sequence of
alpha-WOLF 8

MAEIGYSVCAKLIEVIGSELIKEICDTWGYKSLLEDLNKTVLTV
RNVLIQAGVMRELTSEQQGFIADLKDVVYDADDLFDKLLTRAE
RKQIDGNEISEKVRRFFSSSNKIGQAYYMSRKVKEIKKQLDEIV
DRHTKFGFSAEFIPVCRERGNERETRSYIDVKNILGRDKDKNDII
DRLLNRNGNEACSFLTIVGAGGLGKTALAQLVFNDERVKIEFH
DLRYWVCVSDQDGGQFDVKEILCKILEVVTKEKVDNSSTLELV
QSQFQEKLRGKKYFLVLDDVWNEDREKWLPLEELLMLGQGGS
KVVVTARSEKTANVIGKRHFYTLECLSPDYSWSLFEMSAFQKG
HEQENHHELVDIGKKIVEKCYNNPLAITVVGSLLYGEEISKWRS
FEMSELAKIGNGDNKILPILKLSYHNLIPSLKSCFSYCAVFPKDH
EIKKEMLIDLWIAQGYVVALDGGQSIEDAAEEHFVILLRRCFFQ
DVKKDEYGDVDSVKIHDLMHDVAQEVGREEICVVNDNTKNL
GDKIRHVHGDVNRYAQRVSLCSHSHKIRSYIGGDCEKRCVDTL
IDKWMCLRMLDLSWSDVKNLPNSIGKLLHLRYLNLSDNRNLKI
LPDAITRLHNLQTLLLKDCRSLKELPKDFCKLVKLRHLDLWGC
DDLIGMPFGMDKLTSLRILPNIVVGRKEQSVDDELKALKGLTEI
KGDIDIKICENYRIVEGMNDTGGAGYLKSMKHLREIGITFDGGC
VNPEAVLATLEPPSNIKSLSIHRFDGKTLPVWGRAEINWAISLSH
LVDIQLWHCRNLQEMPVLSKLPHLKSLELYNLISLEYMESTSRS
SSSDTEAATPELPTFFPSLEKLTLWGLEKLKGLGNRRSSSFPRLS
ELKIMECPDLTWFPPCPSLEKLTLWRLDKLKGFGNRRSSTFPRL
SELEIKKCPDLTSFPSCPSLEKLELKESNEALQIIVKITTRGKEKE
ENNNAGVRNSQDDDKVKLRKMVIDNLGYLKSLPTNCLTHLDL

TABLE 2-continued

Sequence information.

|  |  |
|---|---|
|  | TISDSKEGEGEWEVGDAFQKCVSSLRSLTIIGNHGINKVKRLSG<br>RTGLEHFTLLESLKLSDIEDQEDEGEDNIIFWKSFPQNLRSLRIK<br>DSDKMTSLPMGMQYLTSLQTLYLHHCYELNSLPEWISSLSSLQ<br>YLRIYYCPALKSLPEAMRNLTSLQTLGISDCPDLVKRCRKPNGK<br>DYPKIQHIPYWSIEHQVITSL |
| SEQ ID NO: 6:<br>protein<br>sequence of<br>alpha-WOLF 8<br>(isoform 1) | MAEIGYSVCAKLIEVIGSELIKEICDTWGYKSLLEDLNKTVLTV<br>RNVLIQAGVMRELTSEQQGFIADLKDVVYDADDLFDKLLTRAE<br>RKQIDGNEISEKVRRFFSSSNKIGQAYYMSRKVKEIKKQLDEIV<br>DRHTKFGFSAEFIPVCRERGNERETRSYIDVKNILGRDKDKNDII<br>DRLLNRNGNEACSFLTIVGAGGLGKTALAQLVFNDERVKIEFH<br>DLRYWVCVSDQDGGQFDVKEILCKILEVVTKEKVDNSSTLELV<br>QSQFQEKLRGKKYFLVLDDVWNEDREKWLPLEELLMLGQGGS<br>KVVVTARSEKTANVIGKRHFYTLECLSPDYSWSLFEMSAFQKG<br>HEQENHHELVDIGKKIVEKCYNNPLAITVVGSLLYGEEISKWRS<br>FEMSELAKIGNGDNKILPILKLSYHNLIPSLKSCFSYCAVFPKDH<br>EIKKEMLIDLWIAQGYVVALDGGQSIEDAAEEHFVILLRRCFFQ<br>DVKKDEYGDVDSVKIHDLMHDVAQEVGREEICVVNDNTKNL<br>GDKIRHVHGDVNRYAQRVSLCSHSHKIRSYIGGDCEKRCVDTL<br>IDKWMCLRMLDLSWSDVKNLPNSIGKLLHLRYLNLSDNRNLKI<br>LPDAITRLHNLQTLLLKDCRSLKELPKDFCKLVKLRHLDLWGC<br>DDLIGMPFGMDKLTSLRILPNIVVGRKEQSVDDELKALKGLTEI<br>KGDIDIKICENYRIVEGMNDTGGAGYLKSMKHLREIGITFDGGC<br>VNPEAVLATLEPPSNIKSLSIHRFDGKTLPVWGRAEINWAISLSH<br>LVDIQLWHCRNLQEMPVLSKLPHLKSLELYNLISLEYMESTSRS<br>SSSDTEAATPELPTFFPSLEKLTLWGLEKLKGLGNRRSSSFPRLS<br>ELKIMECPDLTWFPPCPSLEKLTLWRLDKLKGFGNRRSSTFPRL<br>SELEIKKCPDLTSFPSCPSLEKLELKESNEALQIIVKITTRGKEKE<br>ENNNAGVRNSQDDDKVKLRKMVIDNLGYLKSLPTNCLTHLDL<br>TISDSKEGEGEWEVGDAFQKCVSSLRSLTIIGNHGINKVKRLSG<br>RTGLEHFTLLESLKLSDIEDQEDEGEDNIIFWKSFPQNLRSLRIK<br>DSDKMTSLPMGMQYLTSLQTLYLHHCYELNSLPEWISSLSSLQ<br>YLRIYYCPALKSLPEAMRNLTSLQTLGISDCPDLVKRCRKPNGK<br>DYPKIQHIPYWSIEHQVLNEYW |
| SEQ ID NO: 7:<br>protein<br>sequence of<br>alpha-WOLF 8<br>(isoform 2) | MAEIGYSVCAKLIEVIGSELIKEICDTWGYKSLLEDLNKTVLTV<br>RNVLIQAGVMRELTSEQQGFIADLKDVVYDADDLFDKLLTRAE<br>RKQIDGNEISEKVRRFFSSSNKIGQAYYMSRKVKEIKKQLDEIV<br>DRHTKFGFSAEFIPVCRERGNERETRSYIDVKNILGRDKDKNDII<br>DRLLNRNGNEACSFLTIVGAGGLGKTALAQLVFNDERVKIEFH<br>DLRYWVCVSDQDGGQFDVKEILCKILEVVTKEKVDNSSTLELV<br>QSQFQEKLRGKKYFLVLDDVWNEDREKWLPLEELLMLGQGGS<br>KVVVTARSEKTANVIGKRHFYTLECLSPDYSWSLFEMSAFQKG<br>HEQENHHELVDIGKKIVEKCYNNPLAITVVGSLLYGEEISKWRS<br>FEMSELAKIGNGDNKILPILKLSYHNLIPSLKSCFSYCAVFPKDH<br>EIKKEMLIDLWIAQGYVVALDGGQSIEDAAEEHFVILLRRCFFQ<br>DVKKDEYGDVDSVKIHDLMHDVAQEVGREEICVVNDNTKNL<br>GDKIRHVHGDVNRYAQRVSLCSHSHKIRSYIGGDCEKRCVDTL<br>IDKWMCLRMLDLSWSDVKNLPNSIGKLLHLRYLNLSDNRNLKI<br>LPDAITRLHNLQTLLLKDCRSLKELPKDFCKLVKLRHLDLWGC<br>DDLIGMPFGMDKLTSLRILPNIVVGRKEQSVDDELKALKGLTEI<br>KGDIDIKICENYRIVEGMNDTGGAGYLKSMKHLREIGITFDGGC<br>VNPEAVLATLEPPSNIKSLSIHRFDGKTLPVWGRAEINWAISLSH<br>LVDIQLWHCRNLQEMPVLSKLPHLKSLELYNLISLEYMESTSRS<br>SSSDTEAATPELPTFFPSLEKLTLWGLEKLKGLGNRRSSSFPRLS<br>ELKIMECPDLTWFPPCPSLEKLTLWRLDKLKGFGNRRSSTFPRL<br>SELEIKKCPDLTSFPSCPSLEKLELKESNEALQIIVKITTRGKEKE<br>ENNNAGVRNSQDDDKVKLRKMVIDNLGYLKSLPTNCLTHLDL<br>TISDSKEGEGEWEVGDAFQKCVSSLRSLTIIGNHGINKVKRLSG<br>RTGLEHFTLLESLKLSDIEDQEDEGEDNIIFWKSFPQNLRSLRIK<br>DSDKMTSLPMGMQYLTSLQTLYLHHCYELNSLPEWISSLSSLQ<br>YLRIYYCPALKSLPEAMRNLTSLQTLGISDCPDLVKRCRKPNGK<br>DYPKIQHIPYWSIEHQLLNTSLILNAPNLQDMD |
| SEQ ID NO: 8:<br>Forward primer<br>LRR domain<br>(Alpha) | ACAAGTGGATGTGTCTTAGG |
| SEQ ID NO: 9:<br>Reverse primer<br>LRR domain | TTCGCCCTCATCTTCCTGG |
| SEQ ID NO: 10:<br>Forward primer<br>LRR domain<br>(Beta) | TCACGTGGGTTGTGTTGT |

TABLE 2-continued

Sequence information.

| | |
|---|---|
| SEQ ID NO: 11:<br>Amplicon of<br>LRR domain of<br>the alpha-<br>WOLF 8 allele | ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGG<br>TTGTGATGATTTGATTGGTATGCCATTTGGAATGGATAAGCT<br>AACTAGTCTTAGAATACTACCAAACATTGTGGTGGGTAGGA<br>AGGAACAAAGTGTTGATGATGAGCTGAAAGCCCTTAAAGGC<br>CTCACCGAGATAAAAGGCGACATTGATATCAAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA<br>CATCGTTTTGATGGTAAAACACTTCCAGTATGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT<br>GATTAGTTTAGAGTACATGGAGAGCACAAGCAGAAGCAGTA<br>GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG<br>CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAA |
| SEQ ID NO: 12:<br>amino acid<br>sequence<br>encoded by<br>amplicon of<br>LRR domain of<br>alpha Wolf 8 | KWMCLRMLDLSWSDVKNLPNSIGKLLHLRYLNLSDNRNLKILP<br>DAITRLHNLQTLLLKDCRSLKELPKDFCKLVKLRHLDLWGCDD<br>LIGMPFGMDKLTSLRILPNIVVGRKEQSVDDELKALKGLTEIKG<br>DIDIKICENYRIVEGMNDTGGAGYLKSMKHLREIGITFDGGCVN<br>PEAVLATLEPPSNIKSLSIHRFDGKTLPVWGRAEINWAISLSHLV<br>DIQLWHCRNLQEMPVLSKLPHLKSLELYNLISLEYMESTSRSSS<br>SDTEAATPELPTFFPSLEKLTLWGLEKLKGLGNRRSSSFPRLSEL<br>KIMECPDLTWFPPCPSLEKLTLWRLDKLKGFGNRRSSTFPRLSE<br>LEIKKCPDLTSFPSCPSLEKLELKESNEALQIIVKITTRGKEKEEN<br>NNAGVRNSQDDDKVKLRKMVIDNLGYLKSLPTNCLTHLDLTIS<br>DSKEGEGEWEVGDAFQKCVSSLRSLTIIGNHGINKVKRLSGRTG<br>LEHFTLLESLKLSDIEDQEDEGE |
| SEQ ID NO: 13:<br>Amplicon of<br>LRR domain of<br>the beta-WOLF<br>0 allele | TCACGTGGGTTGTGTTGTCGATAGAGATCCAGAAATAGTCTT<br>TTTATGTAGCAATAAGATTCGTTCGTATATTAGCGGTCGCTG<br>CATAAAGAATCCGTGGATTCACAAATAGACAACTGGATGT<br>GCCTTAGGGTGTTGGACTTGTCAGATTCATGTGTTAAAGATT<br>TGTCTGATTCAATAGGTAAGCTGCTGCACTTAAGGTATCTTA<br>ACCTCTCTTCTAATATAAAGTTGGAGATAATCCCTGATGCAA<br>TTACAAGACTGCATAACTTGCAGACACTACTTTTAGAAGATT<br>GCAGAAGTTTAAAGGAGTTGCCAAAAGATTTTTGCAAATTG<br>GTCAAACTGAGGCACTTGGAATTACAGGGTTGTCATGATTTG<br>ATTGGTATGTCATTTGGAATGGATAAGCTAACTAGTCTTAGA<br>ATACTACCAAACATTGTGGTGGGTAGGAAGGAACAAAGTGT<br>TGATGATGAGCTGAAAGCCCTAAAAGGCCTCACCGAGATAA<br>AAGGCTCCATTGATATCACAATCTATTCAAAATATAGAAGA<br>GTTGAAGGCATGAATGGCACAGGAGGAGGAGCTGGGTATTT<br>GAAGAGCATGAAACATCTCACGGGGGTTAATATTACATTTG<br>ATGAAGGTGGATGTGTTAACCCTGAAGCTGTGTATTTGAAG<br>AGCATGAAACATCTCACGAGGGTTATTATTATATTTGATTAT<br>AAAGGTGGATGTGTTAACCCTGAAGCTGTGTTGGCAACCCT<br>AGAGCCACCTTCAAATATCAAGAGGTTAGAGATGTGGCATT<br>ACAGTGGTACAACAATTCCAGTATGGGAAGAGCAGAGATT<br>AATTGGGCAATCTCCCTCTCACATCTTGTCGACATCACGCTT<br>GAAGATTGTTACAATTTGCAGGAGATGCCAGTGCTGAGTAA<br>ACTGCCTCATTTGAAATCACTGGAACTTACAGAGTTGGATAA<br>CTTAGAGTACATGGAGAGTAGAAGCAGCAGCAGTAGCAGTG<br>ACACAGAAGCAGCAACACCAGAATTACCAACATTCTTCCCT<br>TCCCTTGAAAAACTTACACTTTGGCGTCTGGACAAGTTGAAG<br>GGTTTTGGGAACAGGAGATCGAGTAGTTTTCCCCGCCTCTCT |

TABLE 2-continued

Sequence information.

```
          AAATTGGAAATCTGGAAATGTCCAGATCTAACGTCATTTCCT
          TCTTGTCCAAGCCTTGAAGAGTTGGAATTGAAAGAAAACAA
          TGAAGCGTTGCAAATAATAGTAAAAATAACAACAACAAGAG
          GTAAAGAAGAAAAAGAAGAAGACAAGAATGCTGGTGTTGG
          AAATTCACAAGATGATGACAATGTCAAATTATGGAAGGTGG
          AAATAGACAATCTGGGTTATCTCAAATCACTGCCCACAAATT
          GTCTGACTCACCTCGACCTTACAATAAGTGATTCCAAGGAGG
          GGGAGGGTGAATGGGAAGTTGGGGATGCATTTCAGAAGTGT
          GTATCTTCTTTGAGAAGCCTCACCATAATCGGAAATCACGGA
          ATAAATAAAGTGAAGAGACTGTCTGGAAGAACAGGGTTGGA
          GCATTTCACTCTGTTGGAATCACTCAAACTTTCAGATATAGA
          AGACCAGGAAGATGAGGGCGAA

SEQ ID NO: 14:   HVGCVVDRDPEIVFLCSNKIRSYISGRCIKNPVDSQIDNWMCLR
amino acid       VLDLSDSCVKDLSDSIGKLLHLRYLNLSSNIKLEIIPDAITRLHNL
sequence         QTLLLEDCRSLKELPKDFCKLVKLRHLELQGCHDLIGMSFGMD
encoded by       KLTSLRILPNIVVGRKEQSVDDELKALKGLTEIKGSIDITIYSKYR
amplicon of      RVEGMNGTGGGAGYLKSMKHLTGVNITFDEGGCVNPEAVYL
LRR domain       KSMKHLTRVIIIFDYKGGCVNPEAVLATLEPPSNIKRLEMWHYS
Beta Wolf 0      GTTIPVWGRAEINWAISLSHLVDITLEDCYNLQEMPVLSKLPHL
(Viroflay)       KSLELTELDNLEYMESRSSSSSSDTEAATPELPTFFPSLEKLTLW
                 RLDKLKGFGNRRSSSFPRLSKLEIWKCPDLTSFPSCPSLEELELK
                 ENNEALQIIVKITTTRGKEEKEEDKNAGVGNSQDDDNVKLWK
                 VEIDNLGYLKSLPTNCLTHLDLTISDSKEGEGEWEVGDAFQKC
                 VSSLRSLTIIGNHGINKVKRLSGRTGLEHFTLLESLKLSDIEDQE
                 DEGE
```

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Testing for Resistance to *Peronospora farinosa* f. sp. *spinaciae* in Spinach Plants The resistance to downy mildew infection was assayed as described by Irish et al. (2008; *Phytopathol.* 98: 894-900), using a differential set. Spinach plants of the invention were sown along with spinach plants from different other genotypes (see Table 3) in trays containing Scotts Redi-Earth medium, and fertilized twice a week after seedling emergence with Osmocote Peter's (13-13-13) fertilizer (Scotts). Plants were inoculated with a sporangial suspension (2.5× $10^5$/ml) of a pathogenic race of *Peronospora farinosa* f sp. *spinaciae* at the first true leaf stage. In this manner, 16 officially recognized pathogenic races were tested.

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants for this specific test were scored as resistant, intermediately resistant, or susceptible based on symptoms of chlorosis and signs of pathogen sporulation on the cotyledons and true leaves, as described by Irish et al. (2007; *Plant Dis.* 91: 1392-1396). Plants exhibiting no evidence of chlorosis and sporulation were in this specific test considered as resistant. Resistant plants were re-inoculated to assess whether plants initially scored as resistant had escaped infection, or whether they were truly resistant. Plants that showed only symptoms of chlorosis, or sporulation occurring only on the tips of the cotyledons were scored as intermediately resistant. Plants showing more than these symptoms of downy mildew infection were scored as being susceptible.

Table 1 shows the resistance of a plant carrying the alpha-WOLF 8 allele to each one of these pathogenic races. Table 3 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(−)", which in practice means a slightly reduced level of infection (with only symptoms of chlorosis, or sporulation only occurring on the tips of the cotyledons in the differential seedling test).

TABLE 3

| | plants | | | | | | | | | | | |
|---|---|---|---|---|---|---|---|---|---|---|---|---|
| Races | Viroflay | Resistoflay | Califlay | Clermont | Campania | Boeing | Lion | Lazio | Whale | Polka | Pigeon | Meerkat |
| Pfs: 1 | + | − | − | − | − | − | − | − | − | − | − | − |
| Pfs: 2 | + | − | + | − | − | − | − | − | − | − | − | − |
| Pfs: 3 | + | + | − | − | − | − | − | − | − | − | − | − |
| Pfs: 4 | + | + | + | − | − | − | − | − | (−) | + | − | − |

TABLE 3-continued

| | plants | | | | | | | | | | | |
|---|---|---|---|---|---|---|---|---|---|---|---|---|
| Races | Viroflay | Resistoflay | Califlay | Clermont | Campania | Boeing | Lion | Lazio | Whale | Polka | Pigeon | Meerkat |
| Pfs: 5 | + | + | − | + | − | − | − | − | − | − | − | − |
| Pfs: 6 | + | + | + | + | + | − | − | − | (−) | + | − | − |
| Pfs: 7 | + | + | + | + | − | − | − | − | (−) | + | − | − |
| Pfs: 8 | + | + | − | + | + | + | − | − | − | − | − | − |
| Pfs: 9 | + | + | − | + | + | − | − | − | − | − | − | − |
| Pfs: 10 | + | + | + | + | + | + | + | − | + | + | − | − |
| Pfs: 11 | + | + | − | + | − | − | − | + | − | − | − | − |
| Pfs: 12 | + | + | − | + | + | + | − | + | − | − | − | − |
| Pfs: 13 | + | + | + | + | (−) | − | − | + | + | (−) | − | − |
| Pfs: 14 | + | + | − | + | + | + | − | + | (−) | − | + | − |
| Pfs: 15 | + | + | + | − | − | − | − | − | + | + | − | − |
| Pfs: 16 | + | + | − | + | − | − | − | + | − | − | + | + |

Example 2: Amplification of the LRR Domain-Encoding Region

The isolated genomic DNA of a spinach plant comprising the alpha-WOLF 8 allele, of which a representative sample of seed was deposited with the NCIMB under NCIMB accession number 42646 was used in polymerase chain reactions (PCR), using forward primer ACAAGTG-GATGTGTCTTAGG (SEQ ID NO:8) and reverse primer TTCGCCCTCATCTTCCTGG (SEQ ID NO:9). The primer pair amplifies the LRR domain-encoding region of an alpha-WOLF gene, and has been designed for selectively amplifying part of a WOLF gene, and not of other CC-NBS-LRR protein-encoding genes.

PCR conditions for amplifying the LRR domain-encoding region of an alpha-WOLF gene using primers having SEQ ID NO:8 and SEQ ID NO:9 were as follows, using Platinum Taq enzyme (Thermo Fisher Scientific):
  3 minutes at 95° C. (initial denaturing step)
  40 amplification cycles, each cycle consisting of: 30 seconds denaturation at 95° C., 30 seconds annealing at 60° C., and 30 seconds extension at 72° C.
  2 minutes at 72° C. (final extension step)

The isolated genomic DNA of a spinach plant of variety Viroflay comprising the beta-WOLF 0 allele was used in polymerase chain reactions (PCR), using forward primer TCACGTGGGTTGTGTTGT (SEQ ID NO:10) and reverse primer TTCGCCCTCATCTTCCTGG (SEQ ID NO:9). The primer pair amplifies the LRR domain-encoding region of a beta-WOLF gene, and has been designed for selectively amplifying part of a WOLF gene, and not of other CC-NBS-LRR protein-encoding genes.

PCR conditions for amplifying the LRR domain-encoding region of a beta-WOLF gene using primers having SEQ ID NO:9 and SEQ ID NO:10 were as follows, using Platinum Taq enzyme (Thermo Fisher Scientific):
  3 minutes at 95° C. (initial denaturing step)
  40 amplification cycles, each cycle consisting of: 30 seconds denaturation at 95° C., 50 seconds annealing at 58° C. and 50 seconds extension at 72° C.
  2 minutes at 72° C. (final extension step)

The PCR products were visualized on agarose gel (not shown), and DNA was purified from the PCR reaction. Subsequently the sequence of the PCR products was determined using methods well known in the art.

The sequence of the LRR domain of the alpha WOLF 8 allele amplified by primers having SEQ ID NO:8 and SEQ ID NO:9 is provided in Table 2 under SEQ ID NO:11.

The sequence of the LRR domain of the beta-WOLF 0 allele amplified by primers having SEQ ID NO:9 and SEQ ID NO:10 is provided in Table 2 under SEQ ID NO:13.

Finally, the obtained sequences were translated into the corresponding amino acid sequence of the LRR domain having SEQ ID NO:12 and SEQ ID NO:14 for the alpha-WOLF 8 allele and the beta-WOLF 0, respectively (See also Table 2).

If PCR products were to be sequenced using SMRT sequencing (Pacific Biosciences), PCR primers and PCR conditions were different.

To the above-mentioned forward primers the following standard amplification sequence was added: GCAGTCGAACATGTAGCTGACTCAGGTCAC (SEQ ID NO:19).

To the reverse primer, the following standard amplification sequence was added: TGGATCACTTGTGCAAGCAT-CACATCGTAG (SEQ ID NO: 20).

Example 3: Introducing Alpha-WOLF 8 Allele in a Plant not Carrying the Allele A spinach plant comprising the alpha-WOLF 8 allele, of which a representative sample of seed was deposited with the NCIMB under NCIMB accession number 42646 was crossed with a plant of variety Viroflay carrying the beta-WOLF 0 allele to obtain a F1 generation. Subsequently, a F1 plant was selfed to obtain a F2 population.

Plants of the F2 population were assayed as described in Example 1 for resistance to *Peronospora farinosa* f. sp. *spinaciae* pfs:15. Approximately 75% of the plants scored completely resistant in the assay.

Genomic DNA of each plant of the same F2 population was isolated and used in two different polymerase chain reactions (PCR). The first PCR reaction was done using primers for amplifying the LRR domain of an alpha-WOLF allele and the second PCR reaction was done using primers for amplifying the LRR domain of a beta-WOLF allele, both as described in Example 2.

The PCR products were visualized on agarose gel (not shown), this demonstrated that approximately 25% of the plant only contained an alpha-WOLF fragment, approximately 50% contained both an alpha- and a beta-WOLF fragment, and that the remaining approximately 25% of the plants only contained a beta-WOLF fragment. The plants containing the alpha-WOLF fragment completely correlated with the plants that scored resistant for pfs:15. The plants only comprising the beta-WOLF fragment completely correlated with the plants that scored susceptible for pfs:15.

DNA from the PCR reaction was purified, and subsequently the sequence of the PCR products was determined. The alpha-WOLF PCR products gave a sequence that corresponded to the sequence of SEQ ID NO:11, the genomic sequence of the LRR domain of the alpha-WOLF 8 allele. The beta-WOLF PCR products gave a sequence that corresponded to the sequence of SEQ ID NO:13 the genomic sequence of the LRR domain of the beta-WOLF 0 allele.

The invention is further described by the following numbered paragraphs:

1. An allele designated alpha-WOLF 8 which confers resistance to at least one *Peronospora farinosa* f. Sp. *spinacea* race when present in a spinach plant, wherein the protein encoded by said allele is a CC-NBS-LRR protein that may comprise in its amino acid sequence: a) the motif "MAEIGYSVC" (SEQ ID NO: 15) at its N-terminus; and b) the motif "KWMCLR" (SEQ ID NO: 16); and wherein the LRR domain of the protein has in order of increased preference at least 92%, 93%, 94%, 95%, 96%, 97%, 98%, 99%, 100% sequence similarity to SEQ ID NO:12.

2. The allele of paragraph 1, wherein the allele when homozygously present in a spinach plant confers complete resistance to *Peronospora farinosa* f. Sp. *spinacea* races pfs:1, pfs:2, pfs:6, pfs:8 and pfs:15, and confers intermediate resistance to pfs:5, pfs:10 and pfs:16, and does not confer resistance to pfs:3, pfs:4, pfs:7, pfs:9, pfs:11, pfs:12, pfs:13 and pfs:14.

3. The allele of paragraph 1 or 2, wherein the allele has a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

4. The allele of paragraph 1 or 2, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

5. The allele of paragraph 1 or 2, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

6. The allele of paragraph 1 or 2, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4.

7. The allele of paragraph 1 or 2, wherein the allele encodes a protein having an amino acid sequence which in order of increased preference has at least 92%, 93%, 94%, 95%, 96%, 97%, 98%, 99%, 100% sequence similarity to SEQ ID NO:5.

8. The allele of paragraph 1 or 2, wherein the allele encodes for a protein having an amino acid sequence which in order of increased preference has at least 92%, 93%, 94%, 95%, 96%, 97%, 98%, 99%, 100% sequence similarity to SEQ ID NO:6.

9. The allele of paragraph 1 or 2, wherein the allele encodes for a protein having an amino acid sequence which in order of increased preference has at least 92%, 93%, 94%, 95%, 96%, 97%, 98%, 99%, 100% sequence similarity to SEQ ID NO:7.

10. A spinach plant comprising the allele of any one of the paragraphs 1 to 9, of which a representative sample of seed capable of growing into a plant comprising said allele was deposited with the NCIMB under NCIMB accession number 42646.

11. The spinach plant of paragraph 10, wherein the plant is an agronomically elite plant.

12. The spinach plant of paragraph 11, wherein the agronomically elite plant is a hybrid variety or an inbred line.

13. The spinach plant of paragraph 11, further comprising a genetic determinant resulting in resistance against *Peronospora farinosa* f. Sp. *spinacea* races pfs:1 to pfs:16.

14. Propagation material capable of developing into and/or being derived from a spinach plant as defined in any of the paragraphs 10 to 13, wherein the propagation material may comprise the allele of any of the paragraphs 1 to 9 and wherein the propagation material is selected from a group consisting of a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

15. Cell of a spinach plant, which cell may comprise the allele of any of the paragraphs 1 to 9.

16. A method of producing a hybrid spinach seed comprising crossing a first parent spinach plant with a second parent spinach plant and harvesting the resultant hybrid spinach seed, wherein said first parent spinach plant may comprise the allele of any of the paragraphs 1 to 9.

17. The method of paragraph 16, wherein the first and/or second parent is a plant of an inbred line.

18. A hybrid spinach plant grown from the seed produced by the method of paragraph 16 or paragraph 17.

19. Method for identifying or selecting a spinach plant carrying the allele of any of the paragraphs 1 to 9, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

20. Method for identifying or selecting a spinach plant carrying the allele of any of the paragraphs 1-4 and 7, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

21. Method for identifying or selecting a spinach plant carrying the allele of any of the paragraphs 1-3, 5 and 8, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

22. Method for identifying or selecting a spinach plant carrying the allele of any of the paragraphs 1-3, 6 and 9, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:4.

23. The method of any of the paragraphs 19 to 22, comprising determining the presence of the LRR domain as defined in paragraph 1.

24. The method of paragraph 23, wherein the LRR domain is determined by using a primer pair to amplify the LRR domain, wherein the forward primer is a nucleic acid molecule having the sequence of SEQ ID NO:8.

25. The method of paragraph 23, wherein the LRR domain is determined by using a primer pair to amplify the LRR domain, wherein the reverse primer is a nucleic acid molecule having the sequence of SEQ ID NO:9.

26. Primer pair comprising a forward primer which is a nucleic acid molecule having the sequence of SEQ ID NO:8 and a reverse primer which is a nucleic acid molecule having the sequence of SEQ ID NO:9.

27. A method for producing a spinach plant showing resistance to *Peronospora farinosa* f. sp. *spinaciae* comprising: (a) crossing a plant comprising the allele of any one of the paragraphs 1 to 9, with another plant; (b) optionally performing one or more rounds of selfing and/or crossing; (c) selecting after one or more rounds of selfing and/or crossing for a plant that may comprise said allele of any of the paragraphs 1 to 9.

28. The method of paragraph 27, wherein the selection of a plant comprising the allele may comprise determining the presence of the allele according the method of anyone of the paragraphs 19 to 25.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying or selecting a spinach plant carrying an allele designated alpha-WOLF 8 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif SEQ ID NO: 15 at its N-terminus; and b) the motif SEQ ID NO: 16; and wherein the LRR domain of the protein has at least 92% sequence identity to SEQ ID NO: 12, comprising determining the presence of a nucleotide sequence or a part thereof in a plant, wherein said sequence has at least 93% sequence identity to SEQ ID NO: 1.

2. A method for identifying or selecting a spinach plant carrying an allele designated alpha-WOLF 8 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif SEQ ID NO: 15 at its N-terminus; and b) the motif SEQ ID NO: 16; and wherein the LRR domain of the protein has at least 92% sequence identity to SEQ ID NO: 12, comprising determining the presence of a nucleotide sequence or a part thereof in a plant, wherein said sequence has least 93% sequence identity to SEQ ID NO: 2.

3. A method for identifying or selecting a spinach plant carrying an allele designated alpha-WOLF 8 which confers resistance to at least one *Peronospora farinosa* f. sp. *spinaciae* race when present in a spinach plant, wherein the protein encoded by said allele is a CC-NBS-LRR protein that comprises in its amino acid sequence: a) the motif SEQ ID NO: 15 at its N-terminus; and b) the motif SEQ ID NO:

16; and wherein the LRR domain of the protein has at least 92% sequence identity to SEQ ID NO: 12, comprising determining the presence of a nucleotide sequence or a part thereof in a plant, wherein said sequence has at least 93%, sequence identity to SEQ ID NO: 3.

4. A method for identifying or selecting a spinach plant carrying the allele of claim 1, comprising determining the presence of a nucleotide sequence or a part thereof in a plant, wherein said sequence has at least 93% sequence identity to SEQ ID NO: 4.

* * * * *

UNITED STATES PATENT AND TRADEMARK OFFICE
CERTIFICATE OF CORRECTION

PATENT NO. : 11,202,421 B2
APPLICATION NO. : 16/361451
DATED : December 21, 2021
INVENTOR(S) : Vincent Laurens Adrianus Kock et al.

It is certified that error appears in the above-identified patent and that said Letters Patent is hereby corrected as shown below:

In the Claims

Column 81, Line 65-Column 82, Lines 52-60, should read:
2. A method for identifying or selecting a spinach plant carrying an allele designated alpha-WOLF 8 which confers resistance to at least one Peronospora farinosa f. sp. spinaciae race when present in a spinach plant, wherein the protein encoded by said allele is a CC-NBS-LRR protein that comprises in its amino acid sequence: a) the motif SEQ ID NO: 15 at its N-terminus; and b) the motif SEQ ID NO: 16; and wherein the LRR domain of the protein has at least 92% sequence identity to SEQ ID NO: 12, comprising determining the presence of a nucleotide sequence or a part thereof in a plant, wherein said sequence has at least 93% sequence identity to SEQ ID NO: 2.

Column 82, Line 61-Column 83, Lines 1-5, should read:
3. A method for identifying or selecting a spinach plant carrying an allele designated alpha-WOLF 8 which confers resistance to at least one Peronospora farinosa f. sp. spinaciae race when present in a spinach plant, wherein the protein encoded by said allele is a CC-NBS-LRR protein that comprises in its amino acid sequence: a) the motif SEQ ID NO: 15 at its N-terminus; and b) the motif SEQ ID NO: 16; and wherein the LRR domain of the protein has at least 92% sequence identity to SEQ ID NO: 12, comprising determining the presence of a nucleotide sequence or a part thereof in a plant, wherein said sequence has at least 93% sequence identity to SEQ ID NO: 3.

Signed and Sealed this
Twelfth Day of July, 2022

Katherine Kelly Vidal
*Director of the United States Patent and Trademark Office*

SEQUENCE LISTING

```
<160> NUMBER OF SEQ ID NOS: 20

<210> SEQ ID NO 1
<211> LENGTH: 8389
<212> TYPE: DNA
<213> ORGANISM: Spinacia oleracea
<220> FEATURE:
<221> NAME/KEY: unsure
<222> LOCATION: 5171..5230
<223> OTHER INFORMATION: /note="n = a or c or t or g"
<220> FEATURE:
<221> NAME/KEY: unsure
<222> LOCATION: 5553..5602
<223> OTHER INFORMATION: /note="n = a or t or c or g"

<400> SEQUENCE: 1
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcgggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta agaagcagtt ggatgaaatt gttgataggc atacaaaatt tgggtttagt     420
gccgagttta tacctgtttg tagggaaagg gggaacgaga gggaaacacg ttcatatata     480
gatgtcaaga atattcttgg gagggataaa gataagaatg atatcataga taggttgctt     540
aatcgtaatg gtaatgaagc ttgtagtttc ctgaccatag tgggagcggg aggattggga     600
aaaactgctc ttgcacaact tgtgttcaat gatgaaaggg tcaaaattga gttccatgat     660
ttgaggtatt gggtttgtgt ctctgatcaa gatgggggcc aatttgatgt gaaagaaatc     720
ctttgtaaga ttttagaggt ggttactaag gagaaagttg ataatagttc cacattggaa     780
ttggtacaaa gccaatttca agagaagtta agaggaaaga agtacttcct tgttcttgat     840
gatgtatgga acgaagatcg tgagaagtgg cttcctttgg aagagttgtt aatgttgggt     900 caaggggaa gcaaggttgt agtgaccgca cgttcagaga agacagcaaa tgtcataggg     960
aaaagacatt tttatacact ggaatgtttg tcaccagatt attcatggag cttatttgaa    1020
atgtcggctt ttcagaaagg gcatgagcag gaaaaccatc acgaactagt tgatattggg    1080
aaaaagattg ttgaaaaatg ttataacaat ccacttgcta taacggtggt aggaagtctt    1140
ctttatggag aggagataag taagtggcgg tcatttgaaa tgagtgagtt ggccaaaatt    1200
ggcaatgggg ataataagat tttgccgata ttaaagctca gttaccataa tcttataccc    1260
```

```
tcgttgaaga gttgcttcag ttattgtgca gtgtttccca aggatcatga aataaagaag   1320
gagatgttga ttgatctttg gatagcacaa ggatacgttg tggcacttga tggaggtcaa   1380
agtatagaag atgctgccga agaacatttt gtaattttgt tacggagatg tttctttcaa   1440
gatgtaaaga aggatgaata tggtgatgtt gattctgtta aaatccacga cttgatgcac   1500
gatgtcgccc aagaagtggg gagggaggaa atatgtgtag tgaatgataa tacaaagaac   1560
ttgggtgata aaatccgtca tgtacatggt gatgtcaata gatatgcaca aagagtctct   1620
ctgtgtagcc atagccataa gattcgttcg tatattggtg gtgattgtga aaaacgttgt   1680
gtggatacac taatagacaa gtggatgtgt cttaggatgt tggacttgtc atggtcggat   1740
gttaaaaatt tgcctaattc aataggtaaa ttgttgcact tgaggtatct taacctgtca   1800
gataatagaa atctaaagat acttcctgat gcaattacaa gactgcataa tttgcagaca   1860
ctgcttttaa aagattgcag aagtttaaag gagttgccaa aagattttg caaattggtc     1920 aaactgagac acttggattt atggggttgt gatgatttga ttggtatgcc atttggaatg   1980
gataagctaa ctagtcttag aatactacca acattgtgg tgggtaggaa ggaacaaagt     2040
gttgatgatg agctgaaagc ccttaaaggc ctcaccgaga taaaggcga cattgatatc     2100 aaaatctgtg aaaattatag aatagttgaa ggcatgaatg acacaggagg agctgggtat   2160
ttgaagagca tgaaacatct cagggagatt ggtattacat tgatggtgg atgtgttaac     2220 cctgaagctg tgttggcaac cctagagcca ccttcaaata tcaagagctt atctatacat   2280
cgttttgatg gtaaaacact tccagtatgg ggaagagcag agattaattg gcaatctcc     2340 ctctcacatc ttgtcgacat ccagctttgg cattgtcgta atttgcagga gatgccagtg   2400
ctgagtaaac tgcctcattt gaaatcactg gaactttata atttgattag tttagagtac   2460
atggagagca caagcagaag cagtagcagt gacacagaag cagcaacacc agaattacca   2520
acattcttcc cttcccttga aaacttaca cttgggggtc tggaaaagtt gaagggtttg      2580
gggaacagga gatcgagtag ttttcccgc ctctctgaat tgaaaatcat ggaatgccca      2640
gatctaacgt ggtttcctcc ctgtccaagc cttgaaaaac ttacactttg gcgtctggac   2700
aagttgaagg gttttgggaa ccggagatcg agtactttc cccgcctctc tgaattggaa      2760
atcaagaaat gcccagatct aacgtcattt ccttcttgtc caagccttga gaagttggaa   2820
ttgaaagaaa gcaatgaagc attgcaaata atagtaaaaa taacaacaag aggtaaagaa   2880
aaagaagaga acaataatgc tggtgttaga aattcacaag atgatgacaa agtcaaatta   2940
cggaagatgg tgatagacaa tctgggttat ctcaaatcac tgcccacaaa ttgtcttact   3000
cacctcgacc ttacaataag tgattccaag gaggggagg gtgaatggga agttggggat   3060
gcatttcaga agtgtgtatc ttcttttgaga agcctcacca taatcggaaa tcacggaata   3120
aataaagtga agagactgtc tggaagaaca gggttggagc atttcactct gttggaatca   3180
ctcaaacttt cagatataga agaccaggaa gatgagggcg aagacaacat catattctgg   3240
aaatcctttc ctcaaaacct ccgcagtttg agaattaaag actctgacaa aatgacaagt   3300
ttgcccatgg ggatgcagta cttaacctcc ctccaaaccc tctatctaca ccattgttat   3360
gaattgaatt cccttccaga atggataagc agcttatcat ctcttcaata cctgcgcata   3420
tactactgtc cagccctgaa atcactacca gaagcaatgc ggaacctcac ctcccttcag   3480
acacttggga tatcggattg tccagaccta gttaaaagat gcagaaaacc caacggcaag   3540
gactatccca aaattcaaca catcccctat tggagtatag aacatcaggt tataactagc   3600
```

-continued

```
ttgtaactaa cttgtaacta cctagtataa atacagtagt ttgtactatt ttacattcaa    3660
ttacacaatt aataaaatgt agactctcac tctctctctc taagccacga gctccaagct    3720
cgtcaatggc ttcccttctc tgttcttgct ttcttctttc ctcttcaatt cacaaattca    3780
acatggtatc agagcgggac gatccttgct cttcacttcc gcacaaaatt ttcgttcaat    3840
tcaacccatc aaattttttt ttttcccccaa attttctcga attcggtcaa aattcgacga    3900
attagggatt caatttaccc tgatttcttc tgattccatt caatgattgt tcatttcgaa    3960
tcttgaatca ataattgtt gattctggat tccccaaatt ctagggttct tgaaggattt     4020
acaagaatct ggcattgctg atagattctt gaagcaattt gcgtctccgt gttcctcggt    4080
ggtcttgagt ttgtttccgt attcgctgct ctcatcttta ctggggattg tggtctgatt    4140
tcttggcttc ctctgtcgat gatgtgattg gtaatactta aaaccctct ctctcttcc     4200 gaaattattg atgctggttc gtcatttttt tttttggaat catctcagtt tatcgccgca    4260
atttgagttg ttgttgggta attgttgttg ctgccgatga tgttttgtga atttgagaat    4320
tgttagaatg attcttgttc aatcaatttg gttctcatac tctaatggaa gcctgttttg    4380
gagcgacgaa ttatgcaatt ctgagatttc ttttgatcct tatttctttt cttcacttga    4440
atttctggtg tttgtgagta attcttggtt aatgtttgat ctgggtagtt cttgggttta    4500
ctgaagacgt tcttgaagg ttttgacaga aaagctgagg tttaattcca aaattcttct     4560
gtccaattac atttttattg ttgatggttc ttatgtgaga actagactga gtttttttta    4620
tgaaattgtt tcgaccttca gatggattcg agagatttga gttcatttc tttgatgaat     4680 gtgttagaaa aggttttggt gcagtgacca ttttaaacca aatagagtta cataaatatt    4740
gggattcttt tctgggaatg tagttaggag ttgaaatctt ttggagctgc tttaccataa    4800
aacccagcct cagagtctgt taaccagtta ggaccgtgta acatgatcc caggctgcat     4860 ttgcgttatc agatttgatt cagttttgga attgtggatt ttgagggttt aaaagcttac    4920
agttgctcct ggagaatggt gtgagcaata taggaattca gcactagtat tgcagaaaat    4980
gaagcttggt tgttgattgt tggcatgttt tgttgccatt gttttgggtt gatgttttcc    5040 tttctttg aatgttggca cgattcaaca tttctttcct gcaacagatt tggagttcag      5100
tacctgtata atcaggtcaa ttttgttcat ttttcccagc aacagatctg gagaatcaga    5160
acctgtaaaa nnnnnnnnnn nnnnnnnnnn nnnnnnnnnn nnnnnnnnnn nnnnnnnnnn    5220
nnnnnnnnnn acccaaagag gtcagttttc attgatccat tgtgatcatt cttttgatga    5280
gacccattga ggctcatttc ttcaaggcaa tattggaagt tgtagattga tatgagcagt    5340
tggtacaaca gcaacaaaag tggccagcat ctatgcttgt tcatgaggag ttcttggtgc    5400
agagttaatg aagagtctgt tttgaagctt tcaaactgaa gatgtttatc accatctcca    5460
gtttgagggg gggtattgga gtatagaaca tcaggttata actagcttgt aactaacttg    5520
taactaccta gtataaatac agtagtttgt acnnnnnnnn nnnnnnnnnn nnnnnnnnnn    5580
nnnnnnnnnn nnnnnnnnnn nnccacgagc tccaagctcg tcaatggctt cccttctctg    5640
ttcttgcttt cttctttcct cttcaattca caaattcaac atccccaaaa ttgtaagtca    5700
ttgcagaaag taatttattc atttatattt atttttatgct tagaatgata tacgcagtcg    5760
tcctttggtt tcaaatcttg aatttggttt ttgttttctt tctttgtttc tttattcaac    5820
accagcccat ttatgattga ttcattaaaa aaaggatgga gttttatgga tttgaagaag    5880
acaacgaatt gagattcctg ggttttcttt tttgttgggg ttggatttca tgtatatgtt    5940
gctgattaaa tacgagactg atgatgatga tgtgtttatg ggttttaaat cagattaaat    6000
```

```
atatgggaaa tgcaagttaa tttgggatgc acataaggtg tttgctgaaa tgtctatgag    6060
aaatgttgtt tcttggactt agaatgatat acactgtcgt cctttggttt ccaatcttac    6120
atttggtttg tgttttctta gtttgtttct ttaatcaaca ccaacccgtt ttttttaaac    6180
tacctgcaac tactaattta cgtttaccct gtatctcagg tactaaatga atattggtga    6240
ttttcagtta ctcaacacta gcttgatcct gaacgcaccc aaccttcagg ttagaatccg    6300
gcttactcat ccttttgtcc agttttcaag taattgtttt ggcaggatca attctctaat    6360
tgttgtacac cgtatattgc aatttatagt gactacagtt aatgaatgtt tacaaaaaat    6420
tagtcatgta aaaacttctt ctctgtccat tacataaact cttttctct ttctaactta     6480 tcatgttcat gtctaaacaa ttaaacatgc tcacatcaat gttcatttaa gctaacttac    6540
ttctgtaaga gagcgagcta gttaaaaact cctttaactt tctgttttat actcaggaca    6600
tggattgatg caagcatgaa gaacttcggg aatttgctaa aactctacca aagcgatgag    6660
agtttggact ttatttcact tgaagtcagg gactgtcaac aaagccacag tgtgcatgtt    6720
ggctgtttca cttggacgat aaaaaggttt atttaattgt tttcctaagt gtatttggct    6780
tacaagcttt tacttttcac ttgaaagggt ttttcttgtt ttaagctttt cgaattagag    6840
ttttcggttg aagtaagagt agtcgtatta gtcttttacc taaggaagac tctttttgt     6900 aattttcaga ctatgcaatt caagttttcg agtgttttct tgcttgtgtg attgtgagtt    6960
ggtgaattcg tctttcatac attttgagat tatcagaagc tttatgctcc accggtagtc    7020
tagtaccttt tctgttactg tgcagggaag taatctggta ccttctatat atatggaaaa    7080
acatacatta tacattatgc aaaattctta caggttagtt acttcctgga acttcattta    7140
cacttagttt ttttgttcc attccctcgg aatcaagtca ttccctctga gaaatatgta     7200
atgaacttct gtatgttgct gtttggttcc tgttttaatc ttcaatttc ttgtatagtt     7260 acagctgcat ttacaatgaa gtttaagcag acactctctt tatatagtgc ctctttctgg    7320
agcaccgtag agctgtctgt ggttgatcac catctgctgc cgagagattc agcaatcgcg    7380
tgtttgatca ggtaaaagtt tttatgtcaa tgtgtttttt tttccgtttg atcaatttat    7440
gtctgtattc agattcttat cttcttacag tagcataaca cattgtttct ttcatttatg    7500
taaactgttt caagattaca gagatgtatg cttcagtcga cattgatgat aacttaagat    7560
ggcattccta caacagttgc aggcgcattc taactccggc aattctagtt aggcaagagg    7620
agcattgcca atacctgcca cctctgggat ttactatacc agggttgaag tttatggaag    7680
acaccagcta tgcacaagcc ttcaagggt catcctacat aacaagttga accaaccaat     7740
tgcttgttgg ttcagtggta attgaagctg aatttggtag ggatggcccg tgttcgatcc    7800
ccacaacaac aattgggagg ggactggaac ctatccacac agaactcgcc ctgaatccgg    7860
attagcccta agggtgaacg gggtgctaac accaaaaaaa aaaacataac aagttgaacc    7920
aaacatactt tgtttgaatt gaagatttag tgatttcatt tgatcgattg agatgtctta    7980
ttataagcgt atatgctctt ggatttggcc acttaggtgt tgtttgacaa ttggacatta    8040
actcgctttt atattttctt ttctcttagg aaaggtgatc ctgagaattt atattggaac    8100 acttttttt tctcactagc tttaaaaaag tgttctgtgt tacctgcaat tcaatttgat     8160 tattttcac atagttttac ctgaaaaagt gttacctgaa aaagtgttac ctgaaaatca     8220
actgacataa gttttgtttt ggatccaatt aaggacacta gataaatcgg aataaataat    8280
caaccaatta agtacttcat aattaaatat gaagtgtatt attatcttat gcttgtgaca    8340
```

```
ttgaaggatg ttatgatatt taactcaat accttgcaaa atatactgg        8389
```

<210> SEQ ID NO 2
<211> LENGTH: 3606
<212> TYPE: DNA
<213> ORGANISM: Spinacia oleracea

<400> SEQUENCE: 2

```
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcggagct actagtgaa       180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgttct tttcctctag taacaagatc ggtcaagctt actacatgtc tcgtaaggtt      360
aaggaaatta gaagcagtt ggatgaaatt gttgataggc atacaaaatt tgggtttagt      420
gccgagttta tacctgtttg tagggaaagg gggaacgaga gggaaacacg ttcatatata     480
gatgtcaaga atattcttgg gagggataaa gataagaatg atatcataga taggttgctt    540
aatcgtaatg gtaatgaagc ttgtagtttc ctgaccatag tgggagcggg aggattggga   600
aaaactgctc ttgcacaact tgtgttcaat gatgaaaggg tcaaaattga gttccatgat    660
ttgaggtatt gggtttgtgt ctctgatcaa gatgggggcc aatttgatgt gaaagaaatc   720
ctttgtaaga ttttagaggt ggttactaag gagaaagttg ataatagttc cacattggaa   780
ttggtacaaa gccaatttca agagaagtta agaggaaaga gtacttcct tgttcttgat    840
gatgtatgga acgaagatcg tgagaagtgg cttcctttgg aagagttgtt aatgttgggt   900
caaggggaa gcaaggttgt agtgaccgca cgttcagaga gacagcaaa tgtcataggg    960
aaaagacatt tttatacact ggaatgtttg tcaccagatt attcatggag cttatttgaa  1020
atgtcggctt tcagaaagg gcatgagcag gaaaaccatc acgaactagt tgatattggg   1080
aaaaagattg ttgaaaaatg ttataacaat ccacttgcta taacggtggt aggaagtctt  1140
ctttatggag aggagataag taagtggcgg tcatttgaaa tgagtgagtt ggccaaaatt  1200
ggcaatgggg ataataagat tttgccgata ttaaagctca gttaccataa tcttatacc   1260
tcgttgaaga gttgcttcag ttattgtgca gtgtttccca aggatcatga aataaagaag  1320
gagatgttga ttgatctttg gatagcacaa ggatacgttg tggcacttga tggaggtcaa  1380
agtatagaag atgctgccga agaacatttt gtaattttgt tacggagatg tttcttttcaa 1440
gatgtaaaga aggatgaata tggtgatgtt gattctgtta aaatccacga cttgatgcac  1500
gatgtcgccc aagaagtggg gagggaggaa atatgtgtag tgaatgataa tacaaagaac  1560
ttgggtgata aaatccgtca tgtacatggt gatgtcaata gatatgcaca aagagtctct  1620
ctgtgtagcc atagccataa gattcgttcg tatattggtg gtgattgtga aaaacgttgt  1680
gtggatacac taatagacaa gtggatgtgt cttaggatgt tggacttgtc atggtcggat  1740
gttaaaaatt tgcctaattc aataggtaaa ttgttgcact tgaggtatct taacctgtca  1800
gataatagaa atctaaagat acttcctgat gcaattacaa gactgcataa tttgcagaca  1860
ctgcttttaa aagattgcag aagtttaaag gagttgccaa aagattttttg caaattggtc  1920
aaactgagac acttggattt atggggttgt gatgatttga ttggtatgcc atttggaatg   1980
gataagctaa ctagtcttag aatactacca aacattgtgg tgggtaggaa ggaacaaagt  2040
gttgatgatg agctgaaagc ccttaaaggc ctcaccgaga taaaaggcga cattgatatc  2100
```

```
aaaatctgtg aaaattatag aatagttgaa ggcatgaatg acacaggagg agctgggtat    2160
ttgaagagca tgaaacatct cagggagatt ggtattacat ttgatggtgg atgtgttaac    2220
cctgaagctg tgttggcaac cctagagcca ccttcaaata tcaagagctt atctatacat    2280
cgttttgatg gtaaaacact tccagtatgg ggaagagcag agattaattg ggcaatctcc    2340
ctctcacatc ttgtcgacat ccagctttgg cattgtcgta atttgcagga gatgccagtg    2400
ctgagtaaac tgcctcattt gaaatcactg gaactttata atttgattag tttagagtac    2460
atggagagca caagcagaag cagtagcagt gacacagaag cagcaacacc agaattacca    2520
acattcttcc cttcccttga aaacttaca ctttggggtc tggaaaagtt gaagggtttg    2580
gggaacagga gatcgagtag ttttccccgc ctctctgaat tgaaaatcat ggaatgccca    2640
gatctaacgt ggtttcctcc ctgtccaagc cttgaaaaac ttacactttg gcgtctggac    2700
aagttgaagg gttttgggaa ccggagatcg agtactttc cccgcctctc tgaattggaa    2760
atcaagaaat gcccagatct aacgtcattt ccttcttgtc caagccttga aagttggaa    2820 ttgaaagaaa gcaatgaagc attgcaaata atagtaaaaa taacaacaag aggtaaagaa    2880
aaagaagaga acaataatgc tggtgttaga aattcacaag atgatgacaa agtcaaatta    2940
cggaagatgg tgatagacaa tctgggttat ctcaaatcac tgcccacaaa ttgtcttact    3000
cacctcgacc ttacaataag tgattccaag gagggggagg gtgaatggga agttggggat    3060
gcatttcaga agtgtgtatc ttctttgaga agcctcacca taatcggaaa tcacggaata    3120
aataaagtga agagactgtc tggaagaaca gggttggagc atttcactct gttggaatca    3180
ctcaaacttt cagatataga agaccaggaa gatgagggcg aagacaacat catattctgg    3240
aaatcctttc ctcaaaacct ccgcagtttg agaattaaag actctgacaa aatgacaagt    3300
ttgcccatgg ggatgcagta cttaacctcc ctccaaaccc tctatctaca ccattgttat    3360
gaattgaatt cccttccaga atggataagc agcttatcat ctcttcaata cctgcgcata    3420
tactactgtc cagccctgaa atcactacca gaagcaatgc ggaacctcac ctcccttcag    3480
acacttggga tatcggattg tccagaccta gttaaaagat gcagaaaacc caacggcaag    3540
gactatccca aaattcaaca catcccctat tggagtatag aacatcaggt tataactagc    3600
ttgtaa                                                              3606

<210> SEQ ID NO 3
<211> LENGTH: 3609
<212> TYPE: DNA
<213> ORGANISM: Spinacia oleracea

<400> SEQUENCE: 3
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcggagct actagtgaa      180 caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta agaagcagtt ggatgaaatt gttgataggc atacaaaatt gggtttagt      420 gccgagttta tacctgtttg tagggaaagg gggaacgaga gggaaacacg ttcatatata     480
gatgtcaaga atattcttgg gagggataaa gataagaatg atatcataga taggttgctt     540
```

```
aatcgtaatg gtaatgaagc ttgtagtttc ctgaccatag tgggagcggg aggattggga      600
aaaactgctc ttgcacaact tgtgttcaat gatgaaaggg tcaaaattga gttccatgat      660
ttgaggtatt gggtttgtgt ctctgatcaa gatgggggcc aatttgatgt gaaagaaatc      720
ctttgtaaga ttttagaggt ggttactaag gagaaagttg ataatagttc cacattggaa      780
ttggtacaaa gccaatttca agagaagtta agaggaaaga agtacttcct tgttcttgat      840
gatgtatgga acgaagatcg tgagaagtgg cttcctttgg aagagttgtt aatgttgggt      900
caagggggaa gcaaggttgt agtgaccgca cgttcagaga agacagcaaa tgtcataggg      960
aaaagacatt tttatacact ggaatgtttg tcaccagatt attcatggag cttatttgaa     1020
atgtcggctt ttcagaaagg gcatgagcag gaaaaccatc acgaactagt tgatattggg     1080
aaaaagattg ttgaaaaatg ttataacaat ccacttgcta taacggtggt aggaagtctt     1140
ctttatggag aggagataag taagtggcgg tcatttgaaa tgagtgagtt ggccaaaatt     1200
ggcaatgggg ataataagat tttgccgata ttaaagctca gttaccataa tcttataccc     1260
tcgttgaaga gttgcttcag ttattgtgca gtgtttccca aggatcatga aataaagaag     1320
gagatgttga ttgatctttg gatagcacaa ggatacgttg tggcacttga tggaggtcaa     1380
agtatagaag atgctgccga agaacatttt gtaattttgt tacggagatg tttctttcaa     1440
gatgtaaaga aggatgaata tggtgatgtt gattctgtta aaatccacga cttgatgcac     1500
gatgtcgccc aagaagtggg gagggaggaa atatgtgtag tgaatgataa tacaaagaac     1560
ttgggtgata aaatccgtca tgtacatggt gatgtcaata gatatgcaca aagagtctct     1620
ctgtgtagcc atagccataa gattcgttcg tatattggtg gtgattgtga aaaacgttgt     1680
gtggatacac taatagacaa gtggatgtgt cttaggatgt tggacttgtc atggtcggat     1740
gttaaaaatt tgcctaattc aataggtaaa ttgttgcact tgaggtatct taacctgtca     1800
gataatagaa atctaaagat acttcctgat gcaattacaa gactgcataa tttgcagaca     1860
ctgcttttaa aagattgcag aagtttaaag gagttgccaa aagattttg caaattggtc       1920 aaactgagac acttggattt atgggggttgt gatgatttga ttggtatgcc atttggaatg     1980
gataagctaa ctagtcttag aatactacca aacattgtgg tgggtaggaa ggaacaaagt     2040
gttgatgatg agctgaaagc ccttaaaggc ctcaccgaga taaaaggcga cattgatatc     2100
aaaatctgtg aaaattatag aatagttgaa ggcatgaatg acacaggagg agctgggtat     2160
ttgaagagca tgaaacatct cagggagatt ggtattacat ttgatggtgg atgtgttaac     2220
cctgaagctg tgttggcaac cctagagcca ccttcaaata tcaagagctt atctatacat     2280
cgttttgatg gtaaaacact tccagtatgg ggaagagcag agattaattg ggcaatctcc     2340
ctctcacatc ttgtcgacat ccagctttgg cattgtcgta atttgcagga gatgccagtg     2400
ctgagtaaac tgcctcatt t gaaatcactg gaactttata atttgattag tttagagtac    2460
atggagagca caagcagaag cagtagcagt gacacagaag cagcaacacc agaattacca    2520
acattcttcc cttcccttga aaaacttaca ctttggggtc tggaaaagtt gaagggtttg    2580
gggaacagga gatcgagtag ttttccccgc ctctctgaat tgaaaatcat ggaatgccca    2640
gatctaacgt ggtttcctcc ctgtccaagc cttgaaaaac ttacactttg gcgtctggac    2700
aagttgaagg gttttgggaa ccggagatcg agtacttttc cccgcctctc tgaattggaa    2760
atcaagaaat gcccagatct aacgtcattt ccttcttgtc caagccttga gaagttggaa    2820
ttgaaagaaa gcaatgaagc attgcaaata atagtaaaaa taacaacaag aggtaaagaa    2880
aaagaagaga acaataatgc tggtgttaga aattcacaag atgatgacaa agtcaaatta    2940
```

-continued

```
cggaagatgg tgatagacaa tctgggttat ctcaaatcac tgcccacaaa ttgtcttact    3000
cacctcgacc ttacaataag tgattccaag gaggggagg gtgaatggga agttggggat    3060
gcatttcaga agtgtgtatc ttctttgaga agcctcacca taatcggaaa tcacggaata    3120
aataaagtga agagactgtc tggaagaaca gggttggagc atttcactct gttggaatca    3180
ctcaaacttt cagatataga agaccaggaa gatgagggcg aagacaacat catattctgg    3240
aaatcctttc ctcaaaacct ccgcagtttg agaattaaag actctgacaa aatgacaagt    3300
ttgcccatgg ggatgcagta cttaacctcc ctccaaaccc tctatctaca ccattgttat    3360
gaattgaatt cccttccaga atggataagc agcttatcat ctcttcaata cctgcgcata    3420
tactactgtc cagccctgaa atcactacca gaagcaatgc ggaacctcac ctcccttcag    3480
acacttggga tatcggattg tccagaccta gttaaaagat gcagaaaacc caacggcaag    3540
gactatccca aaattcaaca catccccctat ggagtatag aacatcaggt actaaatgaa    3600
tattggtga                                                           3609
```

<210> SEQ ID NO 4
<211> LENGTH: 3642
<212> TYPE: DNA
<213> ORGANISM: Spinacia oleracea

<400> SEQUENCE: 4

```
atggccgaaa tcggatactc ggtttgtgcg aaactcatcg aagtgattgg cagtgagctg      60
atcaaagaga tttgtgacac atggggttac aaatctcttc ttgaggacct caacaaaact     120
gtattgacgg tcaggaacgt tctcattcaa gccggggtga tgcgggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta agaagcagtt ggatgaaatt gttgataggc atacaaaatt tgggtttagt     420
gccgagttta tacctgtttg tagggaaagg gggaacgaga gggaaacacg ttcatatata     480
gatgtcaaga atattcttgg gagggataaa gataagaatg atatcataga taggttgctt     540
aatcgtaatg gtaatgaagc ttgtagtttc ctgaccatag tgggagcggg aggattggga     600
aaaactgctc ttgcacaact tgtgttcaat gatgaaaggg tcaaaattga gttccatgat     660
ttgaggtatt gggtttgtgt ctctgatcaa gatgggggcc aatttgatgt gaaagaaatc     720
ctttgtaaga ttttagaggt ggttactaag gagaaagttg ataatagttc cacattggaa     780
ttggtacaaa gccaatttca agagaagtta agaggaaaga agtacttcct tgttcttgat     840
gatgtatgga cgaagatcg tgagaagtgg cttcctttgg aagagttgtt aatgttgggt     900 caaggggaa gcaaggttgt agtgaccgca cgttcagaga agacagcaaa tgtcataggg     960
aaaagacatt tttatacact ggaatgtttg tcaccagatt attcatggag cttatttgaa    1020
atgtcggctt tcagaaagg gcatgagcag gaaaaccatc acgaactagt tgatattggg    1080
aaaaagattg ttgaaaaatg ttataacaat ccacttgcta taacggtggt aggaagtctt    1140
ctttatggag aggagataag taagtggcgg tcatttgaaa tgagtgagtt ggccaaaatt    1200
ggcaatgggg ataataagat tttgccgata ttaaagctca gttaccataa tcttataccc    1260
tcgttgaaga gttgcttcag ttattgtgca gtgtttccca aggatcatga aataaagaag    1320
gagatgttga ttgatctttg gatagcacaa ggatacgttg tggcacttga tggaggtcaa    1380
```

```
agtatagaag atgctgccga agaacatttt gtaattttgt tacggagatg tttctttcaa      1440
gatgtaaaga aggatgaata tggtgatgtt gattctgtta aaatccacga cttgatgcac      1500
gatgtcgccc aagaagtggg gagggaggaa atatgtgtag tgaatgataa tacaaagaac      1560
ttgggtgata aaatccgtca tgtacatggt gatgtcaata gatatgcaca aagagtctct      1620
ctgtgtagcc atagccataa gattcgttcg tatattggtg gtgattgtga aaaacgttgt      1680
gtggatacac taatagacaa gtggatgtgt cttaggatgt tggacttgtc atggtcggat      1740
gttaaaaatt tgcctaattc aataggtaaa ttgttgcact tgaggtatct taacctgtca      1800
gataatagaa atctaaagat acttcctgat gcaattacaa gactgcataa tttgcagaca      1860
ctgcttttaa aagattgcag aagtttaaag gagttgccaa aagattttg caaattggtc       1920
aaactgagac acttggattt atggggttgt gatgatttga ttggtatgcc atttggaatg      1980
gataagctaa ctagtcttag aatactacca aacattgtgg tgggtaggaa ggaacaaagt      2040
gttgatgatg agctgaaagc ccttaaaggc ctcaccgaga taaaggcga cattgatatc       2100
aaaatctgtg aaaattatag aatagttgaa ggcatgaatg acacaggagg agctgggtat      2160
ttgaagagca tgaaacatct cagggagatt ggtattacat ttgatggtgg atgtgttaac      2220
cctgaagctg tgttggcaac cctagagcca ccttcaaata tcaagagctt atctatacat      2280
cgttttgatg gtaaaacact tccagtatgg ggaagagcag agattaattg gcaatctcc       2340
ctctcacatc ttgtcgacat ccagctttgg cattgtcgta atttgcagga gatgccagtg      2400
ctgagtaaac tgcctcattt gaaatcactg gaactttata atttgattag tttagagtac      2460
atggagagca caagcagaag cagtagcagt gacacagaag cagcaacacc agaattacca      2520
acattcttcc cttcccttga aaaacttaca cttttggggtc tggaaaagtt aagggtttg      2580
gggaacagga gatcgagtag ttttcccgc ctctctgaat tgaaaatcat ggaatgccca       2640
gatctaacgt ggtttcctcc ctgtccaagc cttgaaaaac ttacactttg gcgtctggac      2700
aagttgaagg gttttgggaa ccggagatcg agtactttc cccgcctctc tgaattggaa       2760
atcaagaaat gcccagatct aacgtcattt ccttcttgtc caagccttga aagttggaa       2820
ttgaaagaaa gcaatgaagc attgcaaata atagtaaaaa taacaacaag aggtaaagaa      2880
aaagaagaga acaataatgc tggtgttaga aattcacaag atgatgacaa agtcaaatta      2940
cggaagatgg tgatagacaa tctgggttat ctcaaatcac tgcccacaaa ttgtcttact      3000
cacctcgacc ttacaataag tgattccaag gaggggagg gtgaatggga agttggggat       3060
gcatttcaga agtgtgtatc ttcttttgaga agcctcacca taatcggaaa tcacggaata      3120
aataaagtga agagactgtc tggaagaaca gggttggagc atttcactct gttggaatca      3180
ctcaaacttt cagatataga agaccaggaa gatgagggcg aagacaacat catattctgg      3240
aaatcctttc ctcaaaacct ccgcagtttg agaattaaag actctgacaa aatgacaagt      3300
ttgcccatgg ggatgcagta cttaacctcc ctccaaaccc tctatctaca ccattgttat      3360
gaattgaatt cccttccaga atggataagc agcttatcat ctcttcaata cctgcgcata      3420
tactactgtc cagccctgaa atcactacca gaagcaatgc ggaacctcac ctcccttcag      3480
acacttggga tatcggattg tccagaccta gttaaaagat gcagaaaacc caacggcaag      3540
gactatccca aaattcaaca catcccctat tggagtatag aacatcagtt actcaacact      3600
agcttgatcc tgaacgcacc caaccttcag gacatggatt ga                        3642
```

<210> SEQ ID NO 5  
<211> LENGTH: 1201

<212> TYPE: PRT
<213> ORGANISM: Spinacia oleracea

<400> SEQUENCE: 5

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Leu Pro Leu Glu Glu Leu Leu Met Leu Gly Gln Gly Gly Ser
    290                 295                 300

Lys Val Val Thr Ala Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335

Ser Leu Phe Glu Met Ser Ala Phe Gln Lys Gly His Glu Gln Glu Asn
            340                 345                 350

His His Glu Leu Val Asp Ile Gly Lys Lys Ile Val Glu Lys Cys Tyr
        355                 360                 365

Asn Asn Pro Leu Ala Ile Thr Val Val Gly Ser Leu Leu Tyr Gly Glu
    370                 375                 380

Glu Ile Ser Lys Trp Arg Ser Phe Glu Met Ser Glu Leu Ala Lys Ile
385                 390                 395                 400
```

```
Gly Asn Gly Asp Asn Lys Ile Leu Pro Ile Leu Lys Leu Ser Tyr His
            405                 410                 415
Asn Leu Ile Pro Ser Leu Lys Ser Cys Phe Ser Tyr Cys Ala Val Phe
            420                 425                 430
Pro Lys Asp His Glu Ile Lys Lys Glu Met Leu Ile Asp Leu Trp Ile
            435                 440                 445
Ala Gln Gly Tyr Val Val Ala Leu Asp Gly Gly Gln Ser Ile Glu Asp
            450                 455                 460
Ala Ala Glu Glu His Phe Val Ile Leu Leu Arg Arg Cys Phe Phe Gln
465                 470                 475                 480
Asp Val Lys Lys Asp Glu Tyr Gly Asp Val Ser Val Lys Ile His
            485                 490                 495
Asp Leu Met His Asp Val Ala Gln Glu Val Gly Arg Glu Glu Ile Cys
            500                 505                 510
Val Val Asn Asp Asn Thr Lys Asn Leu Gly Asp Lys Ile Arg His Val
            515                 520                 525
His Gly Asp Val Asn Arg Tyr Ala Gln Arg Val Ser Leu Cys Ser His
            530                 535                 540
Ser His Lys Ile Arg Ser Tyr Ile Gly Gly Asp Cys Glu Lys Arg Cys
545                 550                 555                 560
Val Asp Thr Leu Ile Asp Lys Trp Met Cys Leu Arg Met Leu Asp Leu
            565                 570                 575
Ser Trp Ser Asp Val Lys Asn Leu Pro Asn Ser Ile Gly Lys Leu Leu
            580                 585                 590
His Leu Arg Tyr Leu Asn Leu Ser Asp Asn Arg Asn Leu Lys Ile Leu
            595                 600                 605
Pro Asp Ala Ile Thr Arg Leu His Asn Leu Gln Thr Leu Leu Leu Lys
            610                 615                 620
Asp Cys Arg Ser Leu Lys Glu Leu Pro Lys Asp Phe Cys Lys Leu Val
625                 630                 635                 640
Lys Leu Arg His Leu Asp Leu Trp Gly Cys Asp Asp Leu Ile Gly Met
            645                 650                 655
Pro Phe Gly Met Asp Lys Leu Thr Ser Leu Arg Ile Leu Pro Asn Ile
            660                 665                 670
Val Val Gly Arg Lys Glu Gln Ser Val Asp Asp Glu Leu Lys Ala Leu
            675                 680                 685
Lys Gly Leu Thr Glu Ile Lys Gly Asp Ile Asp Ile Lys Ile Cys Glu
            690                 695                 700
Asn Tyr Arg Ile Val Glu Gly Met Asn Asp Thr Gly Gly Ala Gly Tyr
705                 710                 715                 720
Leu Lys Ser Met Lys His Leu Arg Glu Ile Gly Ile Thr Phe Asp Gly
            725                 730                 735
Gly Cys Val Asn Pro Glu Ala Val Leu Ala Thr Leu Glu Pro Pro Ser
            740                 745                 750
Asn Ile Lys Ser Leu Ser Ile His Arg Phe Asp Gly Lys Thr Leu Pro
            755                 760                 765
Val Trp Gly Arg Ala Glu Ile Asn Trp Ala Ile Ser Leu Ser His Leu
            770                 775                 780
Val Asp Ile Gln Leu Trp His Cys Arg Asn Leu Gln Glu Met Pro Val
785                 790                 795                 800
Leu Ser Lys Leu Pro His Leu Lys Ser Leu Glu Leu Tyr Asn Leu Ile
            805                 810                 815
```

```
Ser Leu Glu Tyr Met Glu Ser Thr Ser Arg Ser Ser Ser Ser Asp Thr
                820                 825                 830
Glu Ala Ala Thr Pro Glu Leu Pro Thr Phe Phe Pro Ser Leu Glu Lys
            835                 840                 845
Leu Thr Leu Trp Gly Leu Glu Lys Leu Lys Gly Leu Gly Asn Arg Arg
        850                 855                 860
Ser Ser Ser Phe Pro Arg Leu Ser Glu Leu Lys Ile Met Glu Cys Pro
865                 870                 875                 880
Asp Leu Thr Trp Phe Pro Pro Cys Pro Ser Leu Glu Lys Leu Thr Leu
                885                 890                 895
Trp Arg Leu Asp Lys Leu Lys Gly Phe Gly Asn Arg Arg Ser Ser Thr
            900                 905                 910
Phe Pro Arg Leu Ser Glu Leu Glu Ile Lys Lys Cys Pro Asp Leu Thr
        915                 920                 925
Ser Phe Pro Ser Cys Pro Ser Leu Glu Lys Leu Glu Leu Lys Glu Ser
    930                 935                 940
Asn Glu Ala Leu Gln Ile Ile Val Lys Ile Thr Thr Arg Gly Lys Glu
945                 950                 955                 960
Lys Glu Glu Asn Asn Asn Ala Gly Val Arg Asn Ser Gln Asp Asp Asp
                965                 970                 975
Lys Val Lys Leu Arg Lys Met Val Ile Asp Asn Leu Gly Tyr Leu Lys
            980                 985                 990
Ser Leu Pro Thr Asn Cys Leu Thr His Leu Asp Leu Thr Ile Ser Asp
        995                 1000                1005
Ser Lys Glu Gly Glu Gly Glu Trp Glu Val Gly Asp Ala Phe Gln Lys
    1010                1015                1020
Cys Val Ser Ser Leu Arg Ser Leu Thr Ile Ile Gly Asn His Gly Ile
1025                1030                1035                1040
Asn Lys Val Lys Arg Leu Ser Gly Arg Thr Gly Leu Glu His Phe Thr
                1045                1050                1055
Leu Leu Glu Ser Leu Lys Leu Ser Asp Ile Glu Asp Gln Glu Asp Glu
            1060                1065                1070
Gly Glu Asp Asn Ile Ile Phe Trp Lys Ser Phe Pro Gln Asn Leu Arg
        1075                1080                1085
Ser Leu Arg Ile Lys Asp Ser Asp Lys Met Thr Ser Leu Pro Met Gly
    1090                1095                1100
Met Gln Tyr Leu Thr Ser Leu Gln Thr Leu Tyr Leu His His Cys Tyr
1105                1110                1115                1120
Glu Leu Asn Ser Leu Pro Glu Trp Ile Ser Ser Leu Ser Ser Leu Gln
                1125                1130                1135
Tyr Leu Arg Ile Tyr Tyr Cys Pro Ala Leu Lys Ser Leu Pro Glu Ala
            1140                1145                1150
Met Arg Asn Leu Thr Ser Leu Gln Thr Leu Gly Ile Ser Asp Cys Pro
        1155                1160                1165
Asp Leu Val Lys Arg Cys Arg Lys Pro Asn Gly Lys Asp Tyr Pro Lys
    1170                1175                1180
Ile Gln His Ile Pro Tyr Trp Ser Ile Glu His Gln Val Ile Thr Ser
1185                1190                1195                1200
Leu

<210> SEQ ID NO 6
<211> LENGTH: 1202
<212> TYPE: PRT
<213> ORGANISM: Spinacia oleracea
```

<400> SEQUENCE: 6

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Asn Lys Ile Gly Gln
            100                 105                 110

Ala Tyr Tyr Met Ser Arg Lys Val Lys Glu Ile Lys Lys Gln Leu Asp
            115                 120                 125

Glu Ile Val Asp Arg His Thr Lys Phe Gly Phe Ser Ala Glu Phe Ile
130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
            195                 200                 205

Phe Asn Asp Glu Arg Val Lys Ile Glu Phe His Asp Leu Arg Tyr Trp
210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
            275                 280                 285

Lys Trp Leu Pro Leu Glu Glu Leu Leu Met Leu Gly Gln Gly Gly Ser
290                 295                 300

Lys Val Val Thr Ala Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335

Ser Leu Phe Glu Met Ser Ala Phe Gln Lys Gly His Glu Gln Glu Asn
            340                 345                 350

His His Glu Leu Val Asp Ile Gly Lys Lys Ile Val Glu Lys Cys Tyr
            355                 360                 365

Asn Asn Pro Leu Ala Ile Thr Val Val Gly Ser Leu Tyr Gly Glu
370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
```

-continued

```
                405                 410                 415
Asn Leu Ile Pro Ser Leu Lys Ser Cys Phe Ser Tyr Cys Ala Val Phe
                420                 425                 430
Pro Lys Asp His Glu Ile Lys Lys Glu Met Leu Ile Asp Leu Trp Ile
                435                 440                 445
Ala Gln Gly Tyr Val Val Ala Leu Asp Gly Gly Gln Ser Ile Glu Asp
                450                 455                 460
Ala Ala Glu Glu His Phe Val Ile Leu Leu Arg Arg Cys Phe Phe Gln
465                 470                 475                 480
Asp Val Lys Lys Asp Glu Tyr Gly Asp Val Asp Ser Val Lys Ile His
                485                 490                 495
Asp Leu Met His Asp Val Ala Gln Glu Val Gly Arg Glu Glu Ile Cys
                500                 505                 510
Val Val Asn Asp Asn Thr Lys Asn Leu Gly Asp Lys Ile Arg His Val
                515                 520                 525
His Gly Asp Val Asn Arg Tyr Ala Gln Arg Val Ser Leu Cys Ser His
                530                 535                 540
Ser His Lys Ile Arg Ser Tyr Ile Gly Gly Asp Cys Glu Lys Arg Cys
545                 550                 555                 560
Val Asp Thr Leu Ile Asp Lys Trp Met Cys Leu Arg Met Leu Asp Leu
                565                 570                 575
Ser Trp Ser Asp Val Lys Asn Leu Pro Asn Ser Ile Gly Lys Leu Leu
                580                 585                 590
His Leu Arg Tyr Leu Asn Leu Ser Asp Asn Arg Asn Leu Lys Ile Leu
                595                 600                 605
Pro Asp Ala Ile Thr Arg Leu His Asn Leu Gln Thr Leu Leu Leu Lys
                610                 615                 620
Asp Cys Arg Ser Leu Lys Glu Leu Pro Lys Asp Phe Cys Lys Leu Val
625                 630                 635                 640
Lys Leu Arg His Leu Asp Leu Trp Gly Cys Asp Asp Leu Ile Gly Met
                645                 650                 655
Pro Phe Gly Met Asp Lys Leu Thr Ser Leu Arg Ile Leu Pro Asn Ile
                660                 665                 670
Val Val Gly Arg Lys Glu Gln Ser Val Asp Asp Glu Leu Lys Ala Leu
                675                 680                 685
Lys Gly Leu Thr Glu Ile Lys Gly Asp Ile Asp Ile Lys Ile Cys Glu
                690                 695                 700
Asn Tyr Arg Ile Val Glu Gly Met Asn Asp Thr Gly Gly Ala Gly Tyr
705                 710                 715                 720
Leu Lys Ser Met Lys His Leu Arg Glu Ile Gly Ile Thr Phe Asp Gly
                725                 730                 735
Gly Cys Val Asn Pro Glu Ala Val Leu Ala Thr Leu Glu Pro Pro Ser
                740                 745                 750
Asn Ile Lys Ser Leu Ser Ile His Arg Phe Asp Gly Lys Thr Leu Pro
                755                 760                 765
Val Trp Gly Arg Ala Glu Ile Asn Trp Ala Ile Ser Leu Ser His Leu
                770                 775                 780
Val Asp Ile Gln Leu Trp His Cys Arg Asn Leu Gln Glu Met Pro Val
785                 790                 795                 800
Leu Ser Lys Leu Pro His Leu Lys Ser Leu Glu Leu Tyr Asn Leu Ile
                805                 810                 815
Ser Leu Glu Tyr Met Glu Ser Thr Ser Arg Ser Ser Ser Ser Asp Thr
                820                 825                 830
```

Glu Ala Ala Thr Pro Glu Leu Pro Thr Phe Phe Pro Ser Leu Glu Lys
            835                 840                 845

Leu Thr Leu Trp Gly Leu Glu Lys Leu Lys Gly Leu Gly Asn Arg Arg
    850                 855                 860

Ser Ser Ser Phe Pro Arg Leu Ser Glu Leu Lys Ile Met Glu Cys Pro
865                 870                 875                 880

Asp Leu Thr Trp Phe Pro Pro Cys Pro Ser Leu Glu Lys Leu Thr Leu
                885                 890                 895

Trp Arg Leu Asp Lys Leu Lys Gly Phe Gly Asn Arg Arg Ser Ser Thr
            900                 905                 910

Phe Pro Arg Leu Ser Glu Leu Glu Ile Lys Lys Cys Pro Asp Leu Thr
            915                 920                 925

Ser Phe Pro Ser Cys Pro Ser Leu Glu Lys Leu Glu Leu Lys Glu Ser
        930                 935                 940

Asn Glu Ala Leu Gln Ile Ile Val Lys Ile Thr Thr Arg Gly Lys Glu
945                 950                 955                 960

Lys Glu Glu Asn Asn Asn Ala Gly Val Arg Asn Ser Gln Asp Asp Asp
                965                 970                 975

Lys Val Lys Leu Arg Lys Met Val Ile Asp Asn Leu Gly Tyr Leu Lys
            980                 985                 990

Ser Leu Pro Thr Asn Cys Leu Thr His Leu Asp Leu Thr Ile Ser Asp
        995                 1000                1005

Ser Lys Glu Gly Glu Gly Glu Trp Glu Val Gly Asp Ala Phe Gln Lys
    1010                1015                1020

Cys Val Ser Ser Leu Arg Ser Leu Thr Ile Ile Gly Asn His Gly Ile
1025                1030                1035                1040

Asn Lys Val Lys Arg Leu Ser Gly Arg Thr Gly Leu Glu His Phe Thr
                1045                1050                1055

Leu Leu Glu Ser Leu Lys Leu Ser Asp Ile Glu Asp Gln Glu Asp Glu
            1060                1065                1070

Gly Glu Asp Asn Ile Ile Phe Trp Lys Ser Phe Pro Gln Asn Leu Arg
        1075                1080                1085

Ser Leu Arg Ile Lys Asp Ser Asp Lys Met Thr Ser Leu Pro Met Gly
    1090                1095                1100

Met Gln Tyr Leu Thr Ser Leu Gln Thr Leu Tyr Leu His His Cys Tyr
1105                1110                1115                1120

Glu Leu Asn Ser Leu Pro Glu Trp Ile Ser Ser Leu Ser Ser Leu Gln
                1125                1130                1135

Tyr Leu Arg Ile Tyr Tyr Cys Pro Ala Leu Lys Ser Leu Pro Glu Ala
            1140                1145                1150

Met Arg Asn Leu Thr Ser Leu Gln Thr Leu Gly Ile Ser Asp Cys Pro
        1155                1160                1165

Asp Leu Val Lys Arg Cys Arg Lys Pro Asn Gly Lys Asp Tyr Pro Lys
    1170                1175                1180

Ile Gln His Ile Pro Tyr Trp Ser Ile Glu His Gln Val Leu Asn Glu
1185                1190                1195                1200

Tyr Trp

<210> SEQ ID NO 7
<211> LENGTH: 1213
<212> TYPE: PRT
<213> ORGANISM: Spinacia oleracea

<400> SEQUENCE: 7

```
Met Ala Glu Ile Gly Tyr Ser Val Cys Ala Lys Leu Ile Glu Val Ile
1               5                   10                  15
Gly Ser Glu Leu Ile Lys Glu Ile Cys Asp Thr Trp Gly Tyr Lys Ser
            20                  25                  30
Leu Leu Glu Asp Leu Asn Lys Thr Val Leu Thr Val Arg Asn Val Leu
                35                  40                  45
Ile Gln Ala Gly Val Met Arg Glu Leu Thr Ser Glu Gln Gln Gly Phe
50                  55                  60
Ile Ala Asp Leu Lys Asp Val Val Tyr Asp Ala Asp Asp Leu Phe Asp
65                  70                  75                  80
Lys Leu Leu Thr Arg Ala Glu Arg Lys Gln Ile Asp Gly Asn Glu Ile
            85                  90                  95
Ser Glu Lys Val Arg Arg Phe Phe Ser Ser Asn Lys Ile Gly Gln
                100                 105                 110
Ala Tyr Tyr Met Ser Arg Lys Val Lys Glu Ile Lys Lys Gln Leu Asp
            115                 120                 125
Glu Ile Val Asp Arg His Thr Lys Phe Gly Phe Ser Ala Glu Phe Ile
130                 135                 140
Pro Val Cys Arg Glu Arg Gly Asn Glu Arg Glu Thr Arg Ser Tyr Ile
145                 150                 155                 160
Asp Val Lys Asn Ile Leu Gly Arg Asp Lys Asp Lys Asn Asp Ile Ile
                165                 170                 175
Asp Arg Leu Leu Asn Arg Asn Gly Asn Glu Ala Cys Ser Phe Leu Thr
            180                 185                 190
Ile Val Gly Ala Gly Gly Leu Gly Lys Thr Ala Leu Ala Gln Leu Val
            195                 200                 205
Phe Asn Asp Glu Arg Val Lys Ile Glu Phe His Asp Leu Arg Tyr Trp
210                 215                 220
Val Cys Val Ser Asp Gln Asp Gly Gly Gln Phe Asp Val Lys Glu Ile
225                 230                 235                 240
Leu Cys Lys Ile Leu Glu Val Thr Lys Glu Lys Val Asp Asn Ser
                245                 250                 255
Ser Thr Leu Glu Leu Val Gln Ser Gln Phe Gln Glu Lys Leu Arg Gly
            260                 265                 270
Lys Lys Tyr Phe Leu Val Leu Asp Asp Val Trp Asn Glu Asp Arg Glu
            275                 280                 285
Lys Trp Leu Pro Leu Glu Glu Leu Leu Met Leu Gly Gln Gly Gly Ser
            290                 295                 300
Lys Val Val Thr Ala Arg Ser Glu Lys Thr Ala Asn Val Ile Gly
305                 310                 315                 320
Lys Arg His Phe Tyr Thr Leu Glu Cys Leu Ser Pro Asp Tyr Ser Trp
            325                 330                 335
Ser Leu Phe Glu Met Ser Ala Phe Gln Lys Gly His Glu Gln Glu Asn
            340                 345                 350
His His Glu Leu Val Asp Ile Gly Lys Lys Ile Val Glu Lys Cys Tyr
            355                 360                 365
Asn Asn Pro Leu Ala Ile Thr Val Val Gly Ser Leu Leu Tyr Gly Glu
370                 375                 380
Glu Ile Ser Lys Trp Arg Ser Phe Glu Met Ser Glu Leu Ala Lys Ile
385                 390                 395                 400
Gly Asn Gly Asp Asn Lys Ile Leu Pro Ile Leu Lys Leu Ser Tyr His
            405                 410                 415
```

Asn Leu Ile Pro Ser Leu Lys Ser Cys Phe Ser Tyr Cys Ala Val Phe
            420                 425                 430

Pro Lys Asp His Glu Ile Lys Lys Glu Met Leu Ile Asp Leu Trp Ile
            435                 440                 445

Ala Gln Gly Tyr Val Val Ala Leu Asp Gly Gly Gln Ser Ile Glu Asp
            450                 455                 460

Ala Ala Glu Glu His Phe Val Ile Leu Leu Arg Arg Cys Phe Phe Gln
465                 470                 475                 480

Asp Val Lys Lys Asp Glu Tyr Gly Asp Val Asp Ser Val Lys Ile His
                    485                 490                 495

Asp Leu Met His Asp Val Ala Gln Glu Val Gly Arg Glu Glu Ile Cys
            500                 505                 510

Val Val Asn Asp Asn Thr Lys Asn Leu Gly Asp Lys Ile Arg His Val
            515                 520                 525

His Gly Asp Val Asn Arg Tyr Ala Gln Arg Val Ser Leu Cys Ser His
            530                 535                 540

Ser His Lys Ile Arg Ser Tyr Ile Gly Gly Asp Cys Glu Lys Arg Cys
545                 550                 555                 560

Val Asp Thr Leu Ile Asp Lys Trp Met Cys Leu Arg Met Leu Asp Leu
                565                 570                 575

Ser Trp Ser Asp Val Lys Asn Leu Pro Asn Ser Ile Gly Lys Leu Leu
            580                 585                 590

His Leu Arg Tyr Leu Asn Leu Ser Asp Asn Arg Asn Leu Lys Ile Leu
            595                 600                 605

Pro Asp Ala Ile Thr Arg Leu His Asn Leu Gln Thr Leu Leu Leu Lys
610                 615                 620

Asp Cys Arg Ser Leu Lys Glu Leu Pro Lys Asp Phe Cys Lys Leu Val
625                 630                 635                 640

Lys Leu Arg His Leu Asp Leu Trp Gly Cys Asp Asp Leu Ile Gly Met
                645                 650                 655

Pro Phe Gly Met Asp Lys Leu Thr Ser Leu Arg Ile Leu Pro Asn Ile
            660                 665                 670

Val Val Gly Arg Lys Glu Gln Ser Val Asp Asp Glu Leu Lys Ala Leu
            675                 680                 685

Lys Gly Leu Thr Glu Ile Lys Gly Asp Ile Asp Ile Lys Ile Cys Glu
            690                 695                 700

Asn Tyr Arg Ile Val Glu Gly Met Asn Asp Thr Gly Gly Ala Gly Tyr
705                 710                 715                 720

Leu Lys Ser Met Lys His Leu Arg Glu Ile Gly Ile Thr Phe Asp Gly
                725                 730                 735

Gly Cys Val Asn Pro Glu Ala Val Leu Ala Thr Leu Glu Pro Pro Ser
            740                 745                 750

Asn Ile Lys Ser Leu Ser Ile His Arg Phe Asp Gly Lys Thr Leu Pro
            755                 760                 765

Val Trp Gly Arg Ala Glu Ile Asn Trp Ala Ile Ser Leu Ser His Leu
            770                 775                 780

Val Asp Ile Gln Leu Trp His Cys Arg Asn Leu Gln Glu Met Pro Val
785                 790                 795                 800

Leu Ser Lys Leu Pro His Leu Lys Ser Leu Glu Leu Tyr Asn Leu Ile
                805                 810                 815

Ser Leu Glu Tyr Met Glu Ser Thr Ser Arg Ser Ser Ser Ser Asp Thr
            820                 825                 830

Glu Ala Ala Thr Pro Glu Leu Pro Thr Phe Phe Pro Ser Leu Glu Lys

```
                835                840                845
Leu Thr Leu Trp Gly Leu Glu Lys Leu Lys Gly Leu Gly Asn Arg Arg
    850                855                860

Ser Ser Ser Phe Pro Arg Leu Ser Glu Leu Lys Ile Met Glu Cys Pro
865                870                875                880

Asp Leu Thr Trp Phe Pro Pro Cys Pro Ser Leu Glu Lys Leu Thr Leu
                    885                890                895

Trp Arg Leu Asp Lys Leu Lys Gly Phe Gly Asn Arg Arg Ser Ser Thr
                900                905                910

Phe Pro Arg Leu Ser Glu Leu Glu Ile Lys Lys Cys Pro Asp Leu Thr
                915                920                925

Ser Phe Pro Ser Cys Pro Ser Leu Glu Lys Leu Glu Leu Lys Glu Ser
            930                935                940

Asn Glu Ala Leu Gln Ile Ile Val Lys Ile Thr Thr Arg Gly Lys Glu
945                950                955                960

Lys Glu Glu Asn Asn Asn Ala Gly Val Arg Asn Ser Gln Asp Asp Asp
                965                970                975

Lys Val Lys Leu Arg Lys Met Val Ile Asp Asn Leu Gly Tyr Leu Lys
            980                985                990

Ser Leu Pro Thr Asn Cys Leu Thr His Leu Asp Leu Thr Ile Ser Asp
    995                1000               1005

Ser Lys Glu Gly Glu Gly Glu Trp Glu Val Gly Asp Ala Phe Gln Lys
    1010               1015               1020

Cys Val Ser Ser Leu Arg Ser Leu Thr Ile Ile Gly Asn His Gly Ile
1025               1030               1035               1040

Asn Lys Val Lys Arg Leu Ser Gly Arg Thr Gly Leu Glu His Phe Thr
                1045               1050               1055

Leu Leu Glu Ser Leu Lys Leu Ser Asp Ile Glu Asp Gln Glu Asp Glu
            1060               1065               1070

Gly Glu Asp Asn Ile Ile Phe Trp Lys Ser Phe Pro Gln Asn Leu Arg
                1075               1080               1085

Ser Leu Arg Ile Lys Asp Ser Asp Lys Met Thr Ser Leu Pro Met Gly
    1090               1095               1100

Met Gln Tyr Leu Thr Ser Leu Gln Thr Leu Tyr Leu His His Cys Tyr
1105               1110               1115               1120

Glu Leu Asn Ser Leu Pro Glu Trp Ile Ser Ser Leu Ser Ser Leu Gln
                1125               1130               1135

Tyr Leu Arg Ile Tyr Tyr Cys Pro Ala Leu Lys Ser Leu Pro Glu Ala
                1140               1145               1150

Met Arg Asn Leu Thr Ser Leu Gln Thr Leu Gly Ile Ser Asp Cys Pro
    1155               1160               1165

Asp Leu Val Lys Arg Cys Arg Lys Pro Asn Gly Lys Asp Tyr Pro Lys
    1170               1175               1180

Ile Gln His Ile Pro Tyr Trp Ser Ile Glu His Gln Leu Leu Asn Thr
1185               1190               1195               1200

Ser Leu Ile Leu Asn Ala Pro Asn Leu Gln Asp Met Asp
                1205               1210

<210> SEQ ID NO 8
<211> LENGTH: 20
<212> TYPE: DNA
<213> ORGANISM: Spinacia oleracea
<220> FEATURE:
<223> OTHER INFORMATION: Forward primer
```

<400> SEQUENCE: 8
acaagtggat gtgtcttagg                                          20

<210> SEQ ID NO 9
<211> LENGTH: 19
<212> TYPE: DNA
<213> ORGANISM: Spinacia oleracea
<220> FEATURE:
<223> OTHER INFORMATION: Reverse primer

<400> SEQUENCE: 9
ttcgccctca tcttcctgg                                           19

<210> SEQ ID NO 10
<211> LENGTH: 18
<212> TYPE: DNA
<213> ORGANISM: Spinacia oleracea
<220> FEATURE:
<223> OTHER INFORMATION: Forward primer

<400> SEQUENCE: 10
tcacgtgggt tgtgttgt                                            18

<210> SEQ ID NO 11
<211> LENGTH: 1526
<212> TYPE: DNA
<213> ORGANISM: Spinacia oleracea
<220> FEATURE:
<223> OTHER INFORMATION: Amplicon

<400> SEQUENCE: 11
acaagtggat gtgtcttagg atgttggact tgtcatggtc ggatgttaaa aatttgccta      60
attcaatagg taaattgttg cacttgaggt atcttaacct gtcagataat agaaatctaa     120
agatacttcc tgatgcaatt acaagactgc ataatttgca gacactgctt ttaaaagatt     180
gcagaagttt aaaggagttg ccaaaagatt tttgcaaatt ggtcaaactg agacacttgg     240
atttatgggg ttgtgatgat tgattggta tgccatttgg aatggataag ctaactagtc      300
ttagaatact accaaacatt gtggtgggta ggaaggaaca aagtgttgat gatgagctga     360
aagcccttaa aggcctcacc gagataaaag gcgacattga tatcaaaatc tgtgaaaatt     420
atagaatagt tgaaggcatg aatgacacag gaggagctgg gtatttgaag agcatgaaac     480
atctcaggga gattggtatt acatttgatg gtggatgtgt taaccctgaa gctgtgttgg     540
caaccctaga gccaccttca aatatcaaga gcttatctat acatcgtttt gatggtaaaa     600
cacttccagt atggggaaga gcagagatta ttgggcaat ctccctctca catcttgtcg      660
acatccagct ttggcattgt cgtaatttgc aggagatgcc agtgctgagt aaactgcctc     720
atttgaaatc actggaactt tataatttga ttagtttaga gtacatggag agcacaagca     780
gaagcagtag cagtgacaca gaagcagcaa caccagaatt accaacattc ttcccttccc     840
ttgaaaaact tacactttgg ggtctggaaa agttgaaggg tttggggaac aggagatcga     900
gtagttttcc ccgcctctct gaattgaaaa tcatggaatg cccagatcta acgtggtttc     960
ctccctgtcc aagccttgaa aaacttacac tttggcgtct ggacaagttg aagggttttg    1020
ggaaccggag atcgagtact tttccccgcc tctctgaatt ggaaatcaag aaatgcccag    1080
atctaacgtc atttccttct tgtccaagcc ttgagaagtt ggaattgaaa gaaagcaatg    1140
aagcattgca ataatagta aaaataacaa caagaggtaa agaaaagaa gagaacaata      1200
atgctggtgt tagaaattca caagatgatg acaaagtcaa attacggaag atggtgatag    1260

```
acaatctggg ttatctcaaa tcactgccca caaattgtct tactcacctc gaccttacaa    1320
taagtgattc caaggagggg gagggtgaat gggaagttgg ggatgcattt cagaagtgtg    1380
tatcttcttt gagaagcctc accataatcg gaaatcacgg aataaataaa gtgaagagac    1440
tgtctggaag aacaggggttg gagcatttca ctctgttgga atcactcaaa ctttcagata    1500
tagaagacca ggaagatgag ggcgaa                                          1526
```

<210> SEQ ID NO 12
<211> LENGTH: 508
<212> TYPE: PRT
<213> ORGANISM: Spinacia oleracea
<220> FEATURE:
<223> OTHER INFORMATION: Amino acid sequence encoded by amplicon

<400> SEQUENCE: 12

```
Lys Trp Met Cys Leu Arg Met Leu Asp Leu Ser Trp Ser Asp Val Lys
1               5                   10                  15

Asn Leu Pro Asn Ser Ile Gly Lys Leu Leu His Leu Arg Tyr Leu Asn
            20                  25                  30

Leu Ser Asp Asn Arg Asn Leu Lys Ile Leu Pro Asp Ala Ile Thr Arg
        35                  40                  45

Leu His Asn Leu Gln Thr Leu Leu Lys Asp Cys Arg Ser Leu Lys
    50                  55                  60

Glu Leu Pro Lys Asp Phe Cys Lys Leu Val Lys Leu Arg His Leu Asp
65                  70                  75                  80

Leu Trp Gly Cys Asp Asp Leu Ile Gly Met Pro Phe Gly Met Asp Lys
                85                  90                  95

Leu Thr Ser Leu Arg Ile Leu Pro Asn Ile Val Val Gly Arg Lys Glu
            100                 105                 110

Gln Ser Val Asp Asp Glu Leu Lys Ala Leu Lys Gly Leu Thr Glu Ile
        115                 120                 125

Lys Gly Asp Ile Asp Ile Lys Ile Cys Glu Asn Tyr Arg Ile Val Glu
    130                 135                 140

Gly Met Asn Asp Thr Gly Gly Ala Gly Tyr Leu Lys Ser Met Lys His
145                 150                 155                 160

Leu Arg Glu Ile Gly Ile Thr Phe Asp Gly Gly Cys Val Asn Pro Glu
                165                 170                 175

Ala Val Leu Ala Thr Leu Glu Pro Pro Ser Asn Ile Lys Ser Leu Ser
            180                 185                 190

Ile His Arg Phe Asp Gly Lys Thr Leu Pro Val Trp Gly Arg Ala Glu
        195                 200                 205

Ile Asn Trp Ala Ile Ser Leu Ser His Leu Val Asp Ile Gln Leu Trp
    210                 215                 220

His Cys Arg Asn Leu Gln Glu Met Pro Val Leu Ser Lys Leu Pro His
225                 230                 235                 240

Leu Lys Ser Leu Glu Leu Tyr Asn Leu Ile Ser Leu Glu Tyr Met Glu
                245                 250                 255

Ser Thr Ser Arg Ser Ser Ser Asp Thr Glu Ala Ala Thr Pro Glu
            260                 265                 270

Leu Pro Thr Phe Phe Pro Ser Leu Glu Lys Leu Thr Leu Trp Gly Leu
        275                 280                 285

Glu Lys Leu Lys Gly Leu Gly Asn Arg Arg Ser Ser Phe Pro Arg
    290                 295                 300

Leu Ser Glu Leu Lys Ile Met Glu Cys Pro Asp Leu Thr Trp Phe Pro
```

```
            305                 310                 315                 320
Pro Cys Pro Ser Leu Glu Lys Leu Thr Leu Trp Arg Leu Asp Lys Leu
                325                 330                 335

Lys Gly Phe Gly Asn Arg Arg Ser Ser Thr Phe Pro Arg Leu Ser Glu
                340                 345                 350

Leu Glu Ile Lys Lys Cys Pro Asp Leu Thr Ser Phe Pro Ser Cys Pro
                355                 360                 365

Ser Leu Glu Lys Leu Glu Leu Lys Glu Ser Asn Glu Ala Leu Gln Ile
            370                 375                 380

Ile Val Lys Ile Thr Thr Arg Gly Lys Glu Lys Glu Asn Asn Asn
385                 390                 395                 400

Ala Gly Val Arg Asn Ser Gln Asp Asp Lys Val Lys Leu Arg Lys
                405                 410                 415

Met Val Ile Asp Asn Leu Gly Tyr Leu Lys Ser Leu Pro Thr Asn Cys
                420                 425                 430

Leu Thr His Leu Asp Leu Thr Ile Ser Asp Ser Lys Glu Gly Glu Gly
                435                 440                 445

Glu Trp Glu Val Gly Asp Ala Phe Gln Lys Cys Val Ser Ser Leu Arg
            450                 455                 460

Ser Leu Thr Ile Ile Gly Asn His Gly Ile Asn Lys Val Lys Arg Leu
465                 470                 475                 480

Ser Gly Arg Thr Gly Leu Glu His Phe Thr Leu Leu Glu Ser Leu Lys
                485                 490                 495

Leu Ser Asp Ile Glu Asp Gln Glu Asp Glu Gly Glu
                500                 505
```

<210> SEQ ID NO 13
<211> LENGTH: 1597
<212> TYPE: DNA
<213> ORGANISM: Spinacia oleracea
<220> FEATURE:
<223> OTHER INFORMATION: Amplicon

<400> SEQUENCE: 13

```
tcacgtgggt tgtgttgtcg atagagatcc agaaatagtc tttttatgta gcaataagat      60
tcgttcgtat attagcggtc gctgcataaa gaatccggtg gattcacaaa tagacaactg     120
gatgtgcctt agggtgttgg acttgtcaga ttcatgtgtt aaagatttgt ctgattcaat     180
aggtaagctg ctgcacttaa ggtatcttaa cctctcttct aatataaagt tggagataat     240
ccctgatgca attacaagac tgcataactt gcagacacta cttttagaag attgcagaag     300
tttaaaggag ttgccaaaag atttttgcaa attggtcaaa ctgaggcact tggaattaca     360
gggttgtcat gatttgattg gtatgtcatt tggaatggat aagctaacta gtcttagaat     420
actaccaaac attgtggtgg gtaggaagga acaaagtgtt gatgatgagc tgaaagccct     480
aaaaggcctc accgagataa aaggctccat tgatatcaca atctattcaa aatatagaag     540
agttgaaggc atgaatggca caggaggagg agctgggtat ttgaagagca tgaaacatct     600
cacgggggtt aatattacat ttgatgaagg tggatgtgtt aaccctgaag ctgtgtattt     660
gaagagcatg aaacatctca cgagggttat tattatattt gattataaag gtggatgtgt     720
taaccctgaa gctgtgttgg caaccctaga gccaccttca aatatcaaga ggttagagat     780
gtggcattac agtggtacaa caattccagt atggggaaga gcagagatta attgggcaat     840
ctccctctca catcttgtcg acatcacgct tgaaagattgt tacaatttgc aggagatgcc     900
agtgctgagt aaactgcctc atttgaaatc actggaactt acagagttgg ataacttaga     960
```

```
gtacatggag agtagaagca gcagcagtag cagtgacaca gaagcagcaa caccagaatt    1020
accaacattc ttcccttccc ttgaaaaact tacactttgg cgtctggaca agttgaaggg    1080
ttttgggaac aggagatcga gtagttttcc ccgcctctct aaattggaaa tctggaaatg    1140
tccagatcta acgtcatttc cttcttgtcc aagccttgaa gagttggaat tgaaagaaaa    1200
caatgaagcg ttgcaaataa tagtaaaaat aacaacaaca agaggtaaag aagaaaaaga    1260
agaagacaag aatgctggtg ttggaaattc acaagatgat gacaatgtca aattatggaa    1320
ggtggaaata gacaatctgg gttatctcaa atcactgccc acaaattgtc tgactcacct    1380
cgaccttaca ataagtgatt ccaaggaggg ggagggtgaa tgggaagttg gggatgcatt    1440
tcagaagtgt gtatcttctt tgagaagcct caccataatc ggaaatcacg gaataaataa    1500
agtgaagaga ctgtctggaa gacagggtt ggagcatttc actctgttgg aatcactcaa    1560
actttcagat atagaagacc aggaagatga gggcgaa                            1597
```

<210> SEQ ID NO 14
<211> LENGTH: 532
<212> TYPE: PRT
<213> ORGANISM: Spinacia oleracea
<220> FEATURE:
<223> OTHER INFORMATION: Amino acid sequence encoded by amplicon

<400> SEQUENCE: 14

```
His Val Gly Cys Val Asp Arg Asp Pro Glu Ile Val Phe Leu Cys
1               5                   10                  15

Ser Asn Lys Ile Arg Ser Tyr Ile Ser Gly Arg Cys Ile Lys Asn Pro
            20                  25                  30

Val Asp Ser Gln Ile Asp Asn Trp Met Cys Leu Arg Val Leu Asp Leu
        35                  40                  45

Ser Asp Ser Cys Val Lys Asp Leu Ser Asp Ser Ile Gly Lys Leu Leu
    50                  55                  60

His Leu Arg Tyr Leu Asn Leu Ser Ser Asn Ile Lys Leu Glu Ile Ile
65                  70                  75                  80

Pro Asp Ala Ile Thr Arg Leu His Asn Leu Gln Thr Leu Leu Leu Glu
                85                  90                  95

Asp Cys Arg Ser Leu Lys Glu Leu Pro Lys Asp Phe Cys Lys Leu Val
            100                 105                 110

Lys Leu Arg His Leu Glu Leu Gln Gly Cys His Asp Leu Ile Gly Met
        115                 120                 125

Ser Phe Gly Met Asp Lys Leu Thr Ser Leu Arg Ile Leu Pro Asn Ile
    130                 135                 140

Val Val Gly Arg Lys Glu Gln Ser Val Asp Asp Glu Leu Lys Ala Leu
145                 150                 155                 160

Lys Gly Leu Thr Glu Ile Lys Gly Ser Ile Asp Ile Thr Ile Tyr Ser
                165                 170                 175

Lys Tyr Arg Arg Val Glu Gly Met Asn Gly Thr Gly Gly Gly Ala Gly
            180                 185                 190

Tyr Leu Lys Ser Met Lys His Leu Thr Gly Val Asn Ile Thr Phe Asp
        195                 200                 205

Glu Gly Gly Cys Val Asn Pro Glu Ala Val Tyr Leu Lys Ser Met Lys
    210                 215                 220

His Leu Thr Arg Val Ile Ile Ile Phe Asp Tyr Lys Gly Gly Cys Val
225                 230                 235                 240

Asn Pro Glu Ala Val Leu Ala Thr Leu Glu Pro Pro Ser Asn Ile Lys
```

```
                245                 250                 255
Arg Leu Glu Met Trp His Tyr Ser Gly Thr Thr Ile Pro Val Trp Gly
            260                 265                 270

Arg Ala Glu Ile Asn Trp Ala Ile Ser Leu Ser His Leu Val Asp Ile
            275                 280                 285

Thr Leu Glu Asp Cys Tyr Asn Leu Gln Glu Met Pro Val Leu Ser Lys
        290                 295                 300

Leu Pro His Leu Lys Ser Leu Glu Leu Thr Glu Leu Asp Asn Leu Glu
305                 310                 315                 320

Tyr Met Glu Ser Arg Ser Ser Ser Ser Ser Asp Thr Glu Ala Ala
                325                 330                 335

Thr Pro Glu Leu Pro Thr Phe Phe Pro Ser Leu Glu Lys Leu Thr Leu
            340                 345                 350

Trp Arg Leu Asp Lys Leu Lys Gly Phe Gly Asn Arg Arg Ser Ser Ser
            355                 360                 365

Phe Pro Arg Leu Ser Lys Leu Glu Ile Trp Lys Cys Pro Asp Leu Thr
        370                 375                 380

Ser Phe Pro Ser Cys Pro Ser Leu Glu Glu Leu Lys Glu Asn
385                 390                 395                 400

Asn Glu Ala Leu Gln Ile Ile Val Lys Ile Thr Thr Arg Gly Lys
                405                 410                 415

Glu Glu Lys Glu Glu Asp Lys Asn Ala Gly Val Gly Asn Ser Gln Asp
            420                 425                 430

Asp Asp Asn Val Lys Leu Trp Lys Val Glu Ile Asp Asn Leu Gly Tyr
        435                 440                 445

Leu Lys Ser Leu Pro Thr Asn Cys Leu Thr His Leu Asp Leu Thr Ile
450                 455                 460

Ser Asp Ser Lys Glu Gly Glu Gly Glu Trp Glu Val Gly Asp Ala Phe
465                 470                 475                 480

Gln Lys Cys Val Ser Ser Leu Arg Ser Leu Thr Ile Ile Gly Asn His
            485                 490                 495

Gly Ile Asn Lys Val Lys Arg Leu Ser Gly Arg Thr Gly Leu Glu His
        500                 505                 510

Phe Thr Leu Leu Glu Ser Leu Lys Leu Ser Asp Ile Glu Asp Gln
            515                 520                 525

Asp Glu Gly Glu
    530

<210> SEQ ID NO 15
<211> LENGTH: 9
<212> TYPE: PRT
<213> ORGANISM: Spinacia oleracea
<220> FEATURE:
<223> OTHER INFORMATION: motif N-terminus

<400> SEQUENCE: 15

Met Ala Glu Ile Gly Tyr Ser Val Cys
1               5

<210> SEQ ID NO 16
<211> LENGTH: 6
<212> TYPE: PRT
```

```
<213> ORGANISM: Spinacia oleracea
<220> FEATURE:
<223> OTHER INFORMATION: motif

<400> SEQUENCE: 16

Lys Trp Met Cys Leu Arg
1               5

<210> SEQ ID NO 17
<211> LENGTH: 8
<212> TYPE: PRT
<213> ORGANISM: Spinacia oleracea
<220> FEATURE:
<223> OTHER INFORMATION: motif

<400> SEQUENCE: 17

His Val Gly Cys Val Val Asp Arg
1               5

<210> SEQ ID NO 18
<211> LENGTH: 9
<212> TYPE: PRT
<213> ORGANISM: Spinacia oleracea
<220> FEATURE:
<223> OTHER INFORMATION: additional motif

<400> SEQUENCE: 18

Asp Gln Glu Asp Glu Gly Glu Asp Asn
1               5

<210> SEQ ID NO 19
<211> LENGTH: 30
<212> TYPE: DNA
<213> ORGANISM: Spinacia oleracea
<220> FEATURE:
<223> OTHER INFORMATION: Standard amplification sequence forward primer

<400> SEQUENCE: 19
gcagtcgaac atgtagctga ctcaggtcac                                    30

<210> SEQ ID NO 20
<211> LENGTH: 30
<212> TYPE: DNA
<213> ORGANISM: Spinacia oleracea
<220> FEATURE:
<223> OTHER INFORMATION: standard amplification sequence reverse primer

<400> SEQUENCE: 20
tggatcactt gtgcaagcat cacatcgtag                                    30
```